(12) United States Patent
Klug et al.

(10) Patent No.: US 9,834,635 B2
(45) Date of Patent: Dec. 5, 2017

(54) POLYMERS BASED ON ARCRYLIC, METHACRYLIC OR ETHACRYLIC AMIDOALKYL SULFONIC ACID OR SALTS AND CARBOXYALKY ACRYLATE, METHACRYLATE OR ETHACRYLATE OR OLIGOMERS OF SAID CARBOXY COMPOUNDS

(75) Inventors: Peter Klug, Grossostheim (DE); Dirk Fischer, Harxheim (DE); Thomas Lindner, Mannheim (DE); Matthias Kunze, Frankfurt (DE); Wiebke Moeller, Bad Soden (DE); Carina Mildner, Frankfurt am Main (DE); Sebastiano Lo Vasco, Glauburg (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 13/258,857

(22) PCT Filed: Mar. 20, 2010

(86) PCT No.: PCT/EP2010/001755
§ 371 (c)(1),
(2), (4) Date: Jan. 3, 2012

(87) PCT Pub. No.: WO2010/108634
PCT Pub. Date: Sep. 30, 2010

(65) Prior Publication Data
US 2012/0100084 A1     Apr. 26, 2012

(30) Foreign Application Priority Data
Mar. 25, 2009 (DE) .......................... 10 2009 014 877

(51) Int. Cl.
| | |
|---|---|
| A61K 31/045 | (2006.01) |
| A61K 31/19 | (2006.01) |
| A61K 31/192 | (2006.01) |
| A61K 31/375 | (2006.01) |
| A61K 31/60 | (2006.01) |
| C08F 230/02 | (2006.01) |
| A61K 8/36 | (2006.01) |
| A61K 8/81 | (2006.01) |
| A61Q 5/02 | (2006.01) |
| A61Q 17/04 | (2006.01) |
| A61Q 19/10 | (2006.01) |
| C08F 220/26 | (2006.01) |

(52) U.S. Cl.
CPC ............. *C08F 230/02* (2013.01); *A61K 8/36* (2013.01); *A61K 8/8158* (2013.01); *A61Q 5/02* (2013.01); *A61Q 17/04* (2013.01); *A61Q 19/10* (2013.01); *C08F 220/26* (2013.01)

(58) Field of Classification Search
CPC ........ A61K 8/36; A61K 8/8158; A61Q 17/04; A61Q 19/10; A61Q 5/02
See application file for complete search history.

(56) References Cited

U.S. PATENT DOCUMENTS

| | | | | |
|---|---|---|---|---|
| 4,284,708 | A | * | 8/1981 | Helling et al. ............... 430/216 |
| 5,104,914 | A | * | 4/1992 | Elton et al. ................... 524/22 |
| 5,185,395 | A | | 2/1993 | Robinson et al. |
| 5,879,718 | A | | 3/1999 | Sebillote-Arnaud |
| 5,891,452 | A | | 4/1999 | Sebillote-Arnaud et al. |
| 5,952,395 | A | | 9/1999 | Lorant |
| 6,120,780 | A | | 9/2000 | Dupuis et al. |

(Continued)

FOREIGN PATENT DOCUMENTS

| | | |
|---|---|---|
| CA | 2 209 060 | 12/1997 |
| DE | 10 2009 014877 | 9/2009 |

(Continued)

OTHER PUBLICATIONS

Guranowski et al. (FEBS Journal, vol. 276, Issue 6, pp. 1546-1553, Published online Feb. 3, 2009).*

(Continued)

*Primary Examiner* — Alma Pipic
(74) *Attorney, Agent, or Firm* — Tod A. Waldrop

(57) ABSTRACT

Water-soluble or water-swellable polymers are described, containing a) 20.0 to 98.99 mole percent of one or more independently recurring structural units of the formula (1) and b) 1.0 to 79.99 mole percent of one or more independently recurring structural units of the formula (2), and c) 0.01 to 8.0 mole percent of one or more independently recurring cross-linking structural units, which are obtained from one or more monomers having at least two olefinic double bonds. The polymers are suitable, for example, as thickeners or yield point formers, in particular in cosmetic, dermatological or pharmaceutical compositions.

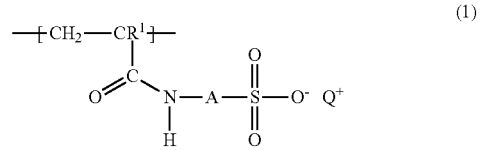

(1)

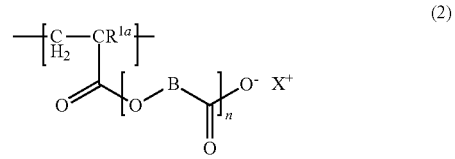

(2)

23 Claims, No Drawings

(56) References Cited

U.S. PATENT DOCUMENTS

| | | | |
|---|---|---|---|
| 6,174,929 B1* | 1/2001 | Hahnle | A61L 15/425 521/149 |
| 6,180,118 B1 | 1/2001 | Maubru | |
| 6,437,068 B2 | 8/2002 | Loffler et al. | |
| 6,468,549 B1 | 10/2002 | Dupuis et al. | |
| 6,509,024 B2 | 1/2003 | Lorant | |
| 6,596,264 B2 | 7/2003 | Terren et al. | |
| 2003/0108497 A1 | 6/2003 | Chevalier et al. | |
| 2007/0166269 A1* | 7/2007 | Cassin et al. | 424/70.16 |
| 2008/0014154 A1 | 1/2008 | Mougin et al. | |
| 2011/0110878 A1 | 5/2011 | Knappe et al. | |
| 2014/0086854 A1 | 3/2014 | Klug et al. | |
| 2014/0127147 A1 | 5/2014 | Klug et al. | |

FOREIGN PATENT DOCUMENTS

| | | |
|---|---|---|
| EP | 0 036 294 | 10/1981 |
| EP | 0 574 202 | 12/1993 |
| EP | 0 699 726 | 3/1996 |
| EP | 0 816 403 | 1/1997 |
| EP | 0 815 828 | 1/1998 |
| EP | 0 815 843 | 1/1998 |
| EP | 0 815 844 | 1/1998 |
| EP | 0 815 845 | 1/1998 |
| EP | 0 815 846 | 1/1998 |
| EP | 0 815 847 | 1/1998 |
| EP | 0 829 258 | 3/1998 |
| EP | 1 116 733 | 7/2001 |
| EP | 1 136 058 | 9/2001 |
| EP | 1 325 729 | 9/2003 |
| EP | 1 468 670 | 10/2004 |
| EP | 1 746 114 | 1/2007 |
| FR | 2 910 899 | 7/2008 |
| JP | 10-081714 A * | 3/1998 |
| WO | WO 90/12822 | 11/1990 |
| WO | WO 2010/009953 | 1/2010 |

OTHER PUBLICATIONS

International Search Report for PCT/EP2010/001755, dated May 21, 2010.
Translation of the Internatonal Preliminary Report on Patentability for PCT/EP2010/001755, dated Sep. 27, 2011.
Safety Data Sheet for "BETA-C", Bimax Chemicals Ltd., London, Unitedd Kingdom, Mar. 8, 2011.
English Abstract for EP0699726, Mar. 6, 1996.
Translation of the Written Opinion of the International Searching Authority for PCT/EP2010/001755, dated Sep. 27, 2011.
English Abstract for EP 1 325 729, Sep. 7, 2003.
English Abstract for EP 1 468 670, Oct. 20, 2004.
English Abstract for FR 2 910 899, Jul. 4, 2008.
International Search Report for PCT/EP2012/000969, dated Aug. 20, 2012.
International Search Report for PCT/EP2012/000968, dated Aug. 20, 2012.

* cited by examiner

POLYMERS BASED ON ARCRYLIC, METHACRYLIC OR ETHACRYLIC AMIDOALKYL SULFONIC ACID OR SALTS AND CARBOXYALKY ACRYLATE, METHACRYLATE OR ETHACRYLATE OR OLIGOMERS OF SAID CARBOXY COMPOUNDS

The present invention relates to crosslinked, water-soluble or water-swellable polymers based on acryl-, methacryl- or ethacrylamidoalkylsulfonic acid or salts thereof and on carboxylalkyl acrylate, methacrylate or ethacrylate or oligomers of these carboxy compounds, to a process for preparing these polymers, to the use of these polymers as thickeners, consistency modifiers or yield point formers, preferably as thickeners or yield point formers in aqueous surfactant systems, or as yield point formers for inorganic particles, organic particles, oil droplets or gas bubbles in surfactant systems, more preferably in cosmetic, dermatological or pharmaceutical compositions, and also to cosmetic, dermatological or pharmaceutical compositions comprising one or more of these polymers.

Polymers based on 2-acrylamido-2-methylpropanesulfonic acid or salts thereof are already known.

For example, crosslinked homopolymers of 2-acrylamido-2-methyl-propanesulfonic acid or salts thereof (Hostacerin® AMPS, Clariant) and also crosslinked copolymers with further monomers such as, for example, vinylpyrrolidone (Aristoflex® AVC, Clariant) can be acquired commercially and are disclosed in EP 0 816 403 and EP 1 116 733. A disadvantage of these polymers, however, is that, in surfactant systems, they do not form clear solutions or sufficient yield points.

Furthermore, hydrophobically modified polymers based on 2-acrylamido-2-methylpropanesulfonic acid or salts thereof can be acquired commercially as well (e.g., Aristoflex® HMB, Clariant) and are described in EP 1 069 142, for example. A disadvantage of these polymers, however, is that only in exceptional cases in surfactant systems do they form a sufficient yield point and clear solutions.

In order to generate the effects described, i.e., in order to form clear solutions and yield points, especially in surfactant systems, the market uses crosslinked polyacrylic acids and copolymers thereof (e.g., Carbopol® Aqua SF1 from Lubrizol). These polymers, however, have the disadvantage that below a pH of around 6 they do not produce any thickening, any yield points or any clear formulations.

Furthermore, the market copolymers based on 2-acrylamido-2-methylpropanesulfonic acid or salts thereof and further monomers selected from acrylic acid and methacrylic acid are obtainable only in the form of oil-containing inverse emulsions (e.g., Simulgel® from Seppic) and are not suitable for use in surfactant systems, since the high oil content leads to turbidities in the surfactant systems.

It was an object of the present invention, therefore, to provide substances which can be used to lessen the disadvantages of the prior-art substances, or even to avoid them, and which can be used in particular, in an advantageous way, for preparing surfactant-containing compositions, such as cosmetic, dermatological or pharmaceutical, surfactant-containing compositions, for example, and hence can be used to obtain clear, surfactant-containing compositions which exhibit a yield point, and in which, in particular, organic and/or inorganic particles and/or oil droplets and also gas bubbles can be stabilized, and which exhibit, within a pH range from 2 to 11, more particularly in acidic pH ranges from 2 to 6, very good rheological properties, at the same time are skin-friendly, and additionally have more advantageous skin sensorial properties in comparison to polyacrylates.

Surprisingly it has now been found that this object is achieved by means of certain crosslinked water-soluble or water-swellable polymers based on acryl-, methacryl- or ethacrylamidoalkylsulfonic acids or salts thereof and carboxyalkyl acrylate, methacrylate or ethacrylate and/or oligomers of these carboxy compounds.

The invention accordingly provides water-soluble or water-swellable polymers comprising a) 20.0 to 98.99 mol %, preferably 20.0 to 98.98 mol %, of one or more independent repeating structural units of the formula (1)

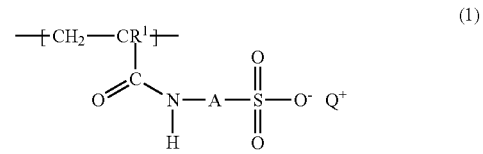

in which $R^1$ is hydrogen, methyl or ethyl,

A is linear or branched $C_1$-$C_{12}$ alkylene, preferably $C_1$-$C_8$ alkylene, and $Q^+$ is $H^+$, $NH_4^+$, organic ammonium ions $[NHR^5R^6R^7]^+$ where $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear monohydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$ or ⅓ $Al^{+++}$ or is mixtures of these ions, and b) 1.0 to 79.99 mol %, preferably 1.0 to 79.98 mol %, of one or more independent repeating structural units of the formula (2)

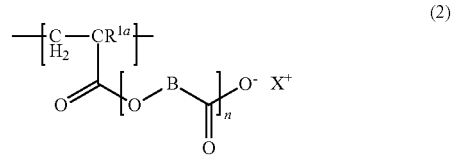

in which $R^{1a}$ is hydrogen, methyl or ethyl, $X^+$ is $H^+$, $NH_4^+$, organic ammonium ions $[NHR^5R^6R^7]^+$ where $R^5$, $R^6$, and $R^7$ independently of one another may be hydrogen, a linear or branched, singularly or multiply unsaturated alkenyl group having 2 to 22 carbon atoms, a $C_6$-$C_{22}$ alkylamidopropyl group, a linear monohydroxyalkyl group having 2 to carbon atoms or a linear or branched di-hydroxyalkyl group having 3 to carbon atoms, and where at least one of the radicals $R^5$, $R^6$, and $R^7$ is not hydrogen, or $X^+$ is $Li^+$, $Na^+$, $K^+$, ½ $Ca^{++}$, ½ $Mg^{++}$, ½ $Zn^{++}$ or ⅓ $Al^{+++}$, or is mixtures of these ions, B is a linear or branched alkylene group having 1 to 6 carbon atoms, and n is an integer from 1 to 10, and c) 0.01 to 8.0 mol %, preferably 0.01 to 5.0 mol %, more preferably 0.01 to 2.0 mol %, and with particular preference 0.25 to 1.5 mol % of one or more independent repeating crosslinking structural units, originating from one or more monomers having at least two olefinic double bonds.

In a polymer of the invention there may in each case be different structural units of the formula (1) and/or of the formula (2). A polymer of the invention may comprise, for example, two or more structural units of the formula (1) which differ from one another in different counterions $Q^+$. A polymer of the invention may also, for example, comprise two or more structural units of the formula (2) which differ from one another in different counterions $X^+$.

The polymers of the invention are, among other things, outstandingly suitable as thickeners and/or yield point formers of aqueous systems and of cosmetic, dermatological or pharmaceutical compositions, and more particularly as thickeners and/or yield point formers of clear aqueous surfactant-containing systems which comprise organic and/or inorganic particles and/or oil droplets and/or gas bubbles. Advantageously they also exhibit good thickening and/or stabilizing properties over a wide pH range, i.e., even at highly acidic pH levels.

Polymers based on 2-carboxyethyl acrylate or its oligomers are likewise already known.

US 2008/0014154 A1 describes copolymers substantially composed of specific structural units containing polyethylene glycol moieties and structural units derived from substantially cationic monomers. These substantially cationic monomers may constitute mixtures of one or more specific cationic monomers and one or more specific anionic monomers. The copolymers are not crosslinked and can be used in cosmetic or pharmaceutical compositions.

EP 0 036 294 A2 discloses oligomers of the formula $CH_2=CH-COO-(CH_2CH_2COO)_nH$, where n possesses average values $\bar{n}$ of greater than 1 to 10, and the use thereof for preparing homopolymers or copolymers. The polymers can be used in coatings and/or impregnating compositions.

EP 0 699 726 A2 describes water-soluble pressure-sensitive adhesives which comprise a water-soluble copolymer synthesized from monomers including 65-95% by weight of a vinylcarboxylic acid.

EP 0 574 202 A1 describes a process for preparing a hydrophilic resin by copolymerizing monomers including a hydrophilic unsaturated monomer with 0.001 to 50 mol %, based on the amount of the monomers, of specific crosslinkers, and subjecting the copolymerization product to heat treatment. The crosslinkers possess structural units $CH_2=CHCOO-(CH_2CH_2COO)_n-$ where n is at least 1. The hydrophilic resin can be used, for example, for preparing absorbent resins for the absorption of liquids, by surface treatment of the hydrophilic resin with a further crosslinker.

US 2007/0166269 A1 describes cosmetic compositions which comprise specific copolymers and are present in the form of water-in-oil emulsions or multiple emulsions. The copolymers include at least one monomer unit derived from at least partly neutralized ionic hydrophilic monomer.

In the one or more structural units of the formula (1) of the polymers of the invention, $R^1$ is preferably hydrogen or methyl and more preferably hydrogen.

In the one or more structural units of the formula (1) of the polymers of the invention, A is preferably a structural unit of the formula $-CH_2-C(CH_3)_2-$.

With particular preference the one or more structural units of the formula (1) of the polymers of the invention derive from 2-acrylamido-2-methylpropanesulfonic acid.

The degree of neutralization of the one or more structural units of the formula (1) of the polymers of the invention is preferably from 50.0 to 100 mol %, more preferably from 80.0 to 100 mol %, with particular preference from 90.0 to 100 mol %, and very preferably from 95.0 to 100 mol %.

In the one or more structural units of the formula (1) of the polymers of the invention, the non-$H^+$ counterion $Q^+$ is preferably selected from $NH_4^+$, alkali$^+$, where alkali$^+$ in turn is preferably $Na^+$, alkaline earth$^{++}$, and mixtures of these ions. With particular preference the non-H counterion $Q^+$ is $NH_4^+$.

In the one or more structural units of the formula (2) of the polymers of the invention, $R^{1a}$ is preferably hydrogen or methyl and more preferably hydrogen.

In the one or more structural units of the formula (2) of the polymers of the invention, B is preferably a structural unit of the formula $-CH_2CH_2-$.

In the one or more structural units of the formula (2) of the polymers of the invention, n is preferably 1 to 5 and more preferably 1 to 4.

The fraction of the one or more structural units of the formula (2) in which n is an integer of 2 or more within component b) of the polymers of the invention is preferably at least 10.0 mol %, more preferably at least 20.0 mol %, with particular preference at least 25.0 mol %, very preferably at least 30.0 mol %, and preferably not more than 70.0 mol %.

With particular preference, in the one or more structural units of the formula (2), B is the group $-CH_2CH_2-$ and n is an integer from 1 to 5 and preferably from 1 to 4.

In the one or more structural units of the formula (2) of the polymers of the invention, the cation $X^+$ is preferably selected from $H^+$, $NH_4^+$, alkali$^+$, with alkali$^+$ in turn being preferably $Na^+$, and from alkaline earth$^{++}$ and mixtures of these ions. With particular preference the counterion $X^+$ is $H^+$ and/or $NH_4^+$.

With particular preference, the non-$H^+$ counterion $Q^+$ in the one or more structural units of the formula (1) is selected from $NH_4^+$, alkali$^+$, where alkali$^+$ in turn is preferably $Na^+$, alkaline earth$^{++}$, and mixtures of these ions, and more preferably is $NH_4^+$, and the counterion $X^+$ in the one or more structural units in the formula (2) is selected from $H^+$, $NH_4^+$, alkali$^+$, where alkali$^+$ in turn is preferably $Na^+$, alkaline earth$^{++}$, and mixtures of these ions, and more preferably is $H^+$ and/or $NH_4^+$.

In another particularly preferred embodiment of the invention, $X^+$ in the one or more structural units of the formula (2) is $H^+$.

In another particularly preferred embodiment of the invention, the polymers of the invention comprise two or more structural units of the formula (2), with the definition of the counterions $X^+$ being $H^+$ in some structural units of the formula (2), and the definition of the counterions $X^+$ being other than $H^+$, and preferably $NH_4^+$, in the other structural units of the formula (2).

In one preferred embodiment of the invention, the molar ratio of the one or more structural units of the formula (1) to the one or more structural units of the formula (2) is from 20:80 to 99:1, more preferably from 50:50 to 97:3, with particular preference from 75:25 to 95:5, and very preferably from 85:15 to 95:5.

The polymers of the invention preferably comprise a) 50.0 to 96.99 mol %, preferably 75.0 to 94.99 mol %, and more preferably 84.75 to 94.75 mol % of the one or more structural units of the formula (1), b) 3.0 to 49.99 mol %, preferably 5.0 to 24.99 mol %, and more preferably 5.0 to 15.0 mol % of the one or more structural units of the formula (2), and c) 0.01 to 5.0 mol %, preferably 0.01 to 2.0 mol %, and more preferably 0.25 to 1.5 mol % of the one or more crosslinking structural units of component c).

In a further preferred embodiment of the invention, the amount of the one or more structural units of the formula (2) in the polymers of the invention is less than or equal to 50% by weight, preferably less than or equal to 45% by weight, based in each case on the total mass of the polymers of the invention.

The one or more crosslinking structural units of component c) of the polymers of the invention derive preferably from acrylic or methacrylic esters, acrylamides or methacrylamides, polyglycol diacrylic or dimethacrylic esters, polyglycol diacrylamides or dimethacrylamides, dipropylene glycol diacrylic or dimethacrylic esters, dipropylene glycol diacrylamides or dimethacrylamides, ethoxylated glycerol diacrylates or dimethacrylates, ethoxylated glycerol triacrylates or trimethacrylates, propoxylated glycerol diacrylates or dimethacrylates, propoxylated glycerol triacrylates or trimethacrylates, or other acrylic or methacrylic esters, acrylamides or methacrylamides of polyfunctional alcohols, trimethylolpropane triacrylates or trimethacrylates, allyl ethers or vinyl ethers of polyfunctional alcohols, methylenebisacrylamide or divinylbenzene.

With further preference the one or more crosslinking structural units of component c) of the polymers of the invention derive from monomers of the general formula (9)

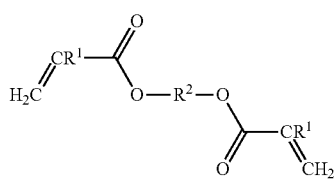

(9)

in which $R^1$ is hydrogen, methyl or ethyl and $R^2$ is a linear or branched alkylene group having 1 to 6 carbon atoms or a linear or branched, singularly or multiply unsaturated alkylene group having 2 to 6 carbon atoms.

With further preference the polymers of the invention comprise one or more independent repeating crosslinking structural units of the formula (3)

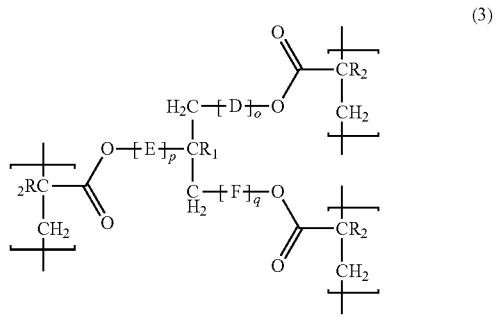

(3)

according to component c), in which $R^1$ and $R^2$ each independently are hydrogen, methyl or ethyl, D, E, and F each independently are methyleneoxy (—$CH_2O$—), ethyleneoxy (—$CH_2$—$CH_2$—O—), propyleneoxy (—$CH(CH_3)$—$CH_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms, and o, p, and q each independently are an integer from 1 to 50.

Particularly preferred as crosslinkers for the polymers of the invention are glycerol propoxylate triacrylate (GPTA), trimethylolpropane triacrylate (TMPTA), pentaerythritol diacrylate monostearate (PEAS), hexanediol diacrylate (HDDA), and hexanediol dimethacrylate (HDDMA). Especially preferred is glycerol propoxylate triacrylate (GPTA).

Particularly preferred polymers of the invention comprise ab) 29.99 to 98.99 mol %, preferably 62.0 to 98.99 mol %, of a mixture of the repeating structural units of the formulae (1) and (2), c) 0.01 to 8.0 mol % of the one or more crosslinking structural units of component c), and d) 0.01 to 70.0 mol %, preferably 1.0 to 70.0 mol %, more preferably 1.0 to 37.99 mol % of one or more independent repeating noncrosslinking structural units, originating from one or more compounds of the formula (4)

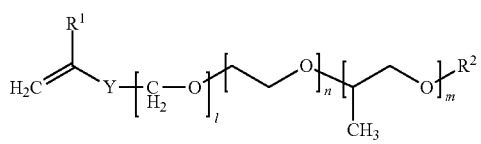

(4)

In which $R^1$ is hydrogen, methyl or ethyl, $R^2$ is H, a linear or branched alkyl group having 1 to 50 carbon atoms, a linear or branched monohydroxyalkyl group having 2 to 6 carbon atoms, a linear or branched dihydroxyalkyl group having 2 to 6 carbon atoms, (—CO—O—$R^7$—)$_o R^8$ or —(CO—$NR^5$—$R^7$)$_p R^8$, l m, n, o, and p each independently are an integer from 0 to 300, Y is a chemical bond, O, $NR^3$, S, $PR^3$, $CH_2$, $CH_2O$, $CH_2NR^3$, $CH_2S$, C(O), C($NR^3$), C(O)O, OC(O), C(O)$NR^3$, $NR^3$C(O), C($NR^4$)$NR^3$, C(O)S, $R^6OC(O)O$, $R^6OC(O)NR^3$, $R^6R^3NC(O)NR^4$, $R^6NR^3C(NR^5)NR^4$, $R^6OC(O)S$, $R^6P(O)O$, $R^6OP(O)O$, $R^6S(O)$, $R^6S(O)(O)$, $R^6S(O)O$, $R^6S(O)(O)O$, $R^6OS(O)O$ or $R^6OS(O)(O)O$, preferably a chemical bond, O, $CH_2$, C(O)O, OC(O), $C(O)NR^3$ or $NR^3C(O)$, $R^3$, $R^4$, $R^5$, and $R^8$ each independently are hydrogen or a linear or branched alkyl radical having 1 to 50 C atoms, $R^6$ is a chemical bond or $CH_2$, and $R^7$ is a linear or branched alkylene radical having 1 to 50 C atoms.

In the one or more compounds of the formula (4), $R^1$ is preferably hydrogen or methyl.

In the one or more compounds of the formula (4), $R^2$ is preferably H, a linear or branched alkyl group having 1 to 50 carbon atoms, a linear or branched monohydroxyalkyl group having 2 to 6 carbon atoms or a linear or branched dihydroxyalkyl group having 2 to 6 carbon atoms.

In the one or more compounds of the formula (4), I is preferably 0.

In the one or more compounds of the formula (4), Y is preferably a chemical bond, O, $CH_2$, C(O)O, OC(O), $C(O)NR^3$ or $NR^3C(O)$.

With particular preference the one or more structural units of component d) are selected from one or more structural units of the formula (5)

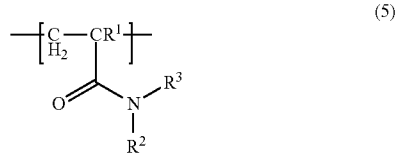

in which
$R^1$ is hydrogen, methyl or ethyl and
$R^2$ and $R^3$ each independently are hydrogen, methyl, ethyl, n-propyl or isopropyl, and at least one of the radicals $R^2$ and $R^3$ is not hydrogen, and
one or more of the structural units of the formula (6)

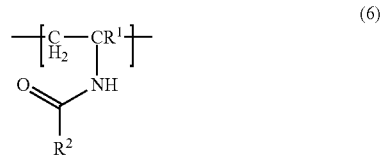

in which
$R^1$ is hydrogen, methyl or ethyl and
$R^2$ is hydrogen, methyl, ethyl, n-propyl or isopropyl.

In one preferred embodiment of the invention, the one or more structural units of component d) are selected from one or more structural units of the formula (5).

In another preferred embodiment of the invention, the one or more structural units of component d) are selected from one or more structural units of the formula (6).

In a further preferred embodiment of the invention, the polymers of invention comprise structural units derived from acrylic acid. Where the polymers of the invention comprise such structural units, they are present preferably in an amount of 0.01 to 10.0 mol % in the polymers of the invention, based on the total mass of the polymers.

In another embodiment of the invention, the polymers of the invention contain no cationic structural units.

The distribution of the different structural units in the polymers of the invention may be random, blocklike, alternating or gradientlike.

The polymers of the invention possess preferably a molecular weight of $10^3$ to $10^9$ g/mol, more preferably of $10^4$ to $10^7$ g/mol, and with particular preference of $10^5$ to $5 \cdot 10^6$ g/mol.

The polymers of the invention are prepared by means of radical polymerization in a protic solvent, preferably in tert-butanol. In this procedure, the corresponding monomers are dispersed or dissolved, for example, in the protic solvent, and the polymerization is initiated conventionally, as for example by addition of a radical-forming compound. In this case it is possible, for example, for the monomers introduced initially to be polymerized "directly". Alternatively, they may be neutralized prior to the polymerization, by reaction, for example, of acidic groups in monomers used with bases prior to the polymerization, forming the counterions $Q^+$ of the structural units of formula (1) or $X^+$ of the structural units of formula (2). Instead of the neutralization of the monomers before the polymerization, however, it is also possible for the polymers to be neutralized with the bases after the polymerization has taken place.

The present invention accordingly further provides a process for preparing the polymers of the invention, wherein monomers from which the structural units of components a) to c) and optionally d) derive and also optionally, further monomers are radically polymerized in a protic solvent, preferably in tert-butanol, and optionally the monomers before the polymerization or the polymer after the polymerization are or is neutralized with ammonia or organic amines or with a base containing $Li^+$, $Na^+$, $K^+$, $Ca^{++}$, $Mg^{++}$, $Zn^{++}$ or $Al^{+++}$, preferably with the corresponding hydroxides or carbonates, and more preferably with hydroxides.

Radical polymerizations are common knowledge to the skilled person and are described comprehensively in standard works of the literature, as for example in "Makromolekulare Chemie: Eine Einführung" [Macromolecular Chemistry: An introduction] by Bernd Tieke, Wiley-VCH, $2^{nd}$ fully revised and expanded edition (Sep. 9, 2005) ISBN-10: 3527313796.

Qualities of the polymers of the invention include good mildness to skin and a pleasant skin feel. Moreover, the polymers of the invention are acid-stable. Since the polymers of the invention thicken even at acidic pH levels, the thickened cosmetic products can advantageously be preserved even with organic acids, such as benzoic acid, sorbic acid or para-methoxybenzoic acid, since sufficient thickener performance is available even at the low pH levels that are necessary. They can be used to obtain clear solutions.

The polymers of the invention are advantageously suitable, moreover, for preparing cosmetic, dermatological or pharmaceutical compositions.

The present invention accordingly further provides the use of one or more polymers of the invention for preparing cosmetic, dermatological or pharmaceutical compositions, and also cosmetic, dermatological or pharmaceutical compositions comprising one or more polymers of the invention.

Based on the completed compositions, the compositions of the invention comprise preferably 0.01% to 10.0% by weight, more preferably 0.1% to 5.0% by weight, and with particular preference 0.5% to 2.0% by weight of the polymers of the invention.

In one preferred embodiment of the invention, the surfactant-containing compositions of the invention have viscosities preferably in the range from 100 to 50 000 mPa·s, more preferably in the range from 100 to 10 000 mPa·s, with particular preference in the range from 500 to 5000 mPa·s, and very preferably in the range from 500 to 4000 mPa·s (25° C., Brookfield RVT, T-C spindle at 5 rpm).

In another preferred embodiment of the invention, the compositions, such as creams, lotions, aqueous and aqueous alcoholic formulations, of the invention have viscosities preferably in the range from 100 to 50 000 mPa·s, more preferably in the range from 500 to 30 000 mPa·s, and with particular preference in the range from 1000 to 20 000 mPa·s (25° C., Brookfield RVT, T-C spindle at 5 rpm).

In a further preferred embodiment of the invention, the compositions of the invention are in the form of fluids, gels, oils, foams, sprays, lotions or creams.

The compositions of the invention are preferably water-based or water/alcohol-based or in the form of oil-in-water emulsions.

In one particularly preferred embodiment of the invention the compositions of the invention are water-based or water/alcohol-based or in the form of oil-in-water emulsions, with particular preference in the form of aqueous, surfactant-containing, or aqueous-alcoholic, surfactant-containing compositions, and preferably comprise, based on the total weight of the compositions,
a) up to 98.0%, preferably 60.0% to 98.0%, more preferably 70.0% to 94.4%, with particular preference 75.0 to 94.5%, by weight, of a water phase or aqueous-alcoholic phase,
b) up to 50.0%, preferably 1.0% to 30.0%, more preferably 5.0% to 20.0%, with particular preference 5.0% to 15.0%, by weight, of one or more surfactants,
c) up to 10.0%, preferably 0.1% to 10.0%, more preferably 0.1% to 5.0%, with particular preference 0.5% to 2.0%, by weight, of one or more of the polymers of the invention, and
d) up to 50.0%, preferably 0.5% to 38.99%, more preferably 0.5% to 6.0%, with particular preference 1.0% to 5.0%, by weight, of one or more further additives, the one or more additives being more particularly one or more oils when the composition of the invention is in the form of oil-in-water emulsions.

For the water/alcohol-based or else alcohol-based compositions of the invention, consideration is given to all monohydric or polyhydric alcohols. Preference is given to alcohols having 1 to 4 carbon atoms such as ethanol, propanol, isopropanol, n-butanol, isobutanol, tert-butanol or glycerol, and also alkylene glycols, more particularly propylene, butylene or hexylene glycol, and mixtures of the stated alcohols. Further preferred alcohols are polyethylene glycols having a relative molecular mass of below 2000. Especially preferred is the use of polyethylene glycol having a relative molecular mass of between 200 and 600, and of polyethylene glycol having a relative molecular mass of between 400 and 600.

The compositions of the invention may comprise one or more oils.

The oils can advantageously be selected from the group of triglycerides, natural and synthetic fatty substances, preferably esters of fatty acids with alcohols of low carbon number, e.g. with methanol, isopropanol, propylene glycol or glycerol, or esters of fatty alcohols with alkanoic acids of low carbon number or with fatty acids or from the group of alkyl benzoates, and also natural or synthetic hydrocarbon oils.

Triglycerides of linear or branched, saturated or unsaturated, optionally hydroxylated, $C_8$-$C_{30}$ fatty acids, in particular vegetable oils, such as sunflower oil, corn oil, soybean oil, rice oil, jojoba oil, babassu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, e.g. the commercial product Myritol® 318, and also the commercial product Velsan® CCT (capric/caprylic triglyceride, Clariant) are suitable. Hydrogenated triglycerides are also inventively preferred. Oils of animal origin, for example beef tallow, perhydrosqualene, lanolin, can also be used A further class of preferred oil bodies is the benzoic acid esters of linear or branched $C_{8-22}$-alkanols, e.g. the commercial products Finsolv® SB (isostearyl benzoate), Finsolv® TN($C_{12}$-$C_{15}$-alkyl benzoate) and Finsolv® EB (ethylhexyl benzoate).

A further class of preferred oil substances is the dialkyl ethers having in total 12 to 36 carbon atoms, in particular having 12 to 24 carbon atoms, such as, for example, di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and di-tert-butyl ether and diisopentyl ether.

Branched saturated or unsaturated fatty alcohols having 6-30 carbon atoms, e.g. isostearyl alcohol, and Guerbet alcohols, are likewise suitable.

A further class of preferred oil substances is hydroxycarboxylic acid alkyl esters. Preferred hydroxycarboxylic acid alkyl esters are full esters of glycolic acid, lactic acid, malic acid, tartaric acid or citric acid. Further esters of hydroxycarboxylic acids which are suitable in principle are esters of β-hydroxypropionic acid, of tartronic acid, of D-gluconic acid, saccharic acid, mucic acid or glucuronic acid. Suitable alcohol components of these esters are primary, linear or branched aliphatic alcohols having 8 to 22 carbon atoms. Here, the esters of $C_{12}$-$C_{15}$ fatty alcohols are particularly preferred. Esters of this type are commercially available, e.g. under the trade name Cosmacol® from EniChem, Augusta Industriale.

A further class of preferred oil substances is dicarboxylic acid esters of linear or branched $C_2$-$C_{10}$-alkanols, such as di-n-butyl adipate (Cetiol® B), di-(2-ethylhexyl) adipate and di-(2-ethylhexyl) succinate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate, and also diisotridecyl azelate.

Likewise preferred oil substances are symmetrical, asymmetrical or cyclic esters of carbonic acid with fatty alcohols, glycerol carbonate or dicaprylyl carbonate (Cetiol® CC).

A further class of preferred oil substances is the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols.

A further class of preferred oil substances is hydrocarbon oils, for example those with linear or branched, saturated or unsaturated $C_7$-$C_{40}$-carbon chains, for example Vaseline, dodecane, isododecane, cholesterol, lanolin, synthetic hydrocarbons such as polyolefins, in particular polyisobutene, hydrogenated polyisobutene, polydecane, and hexadecane, isohexadecane, paraffin oils, isoparaffin oils, e.g. the commercial products of the Permethyl® series, squalane, squalene, and alicyclic hydrocarbons, e.g. the commercial product 1,3-di(2-ethylhexyl)cyclohexane (Cetiol® S), ozokerite, and ceresine.

Silicone oils and silicone waxes are also suitable preferably dimethylpolysiloxanes and cyclomethicones, polydialkylsiloxanes $R_3SiO(R_2SiO)_xSiR_3$, where R is methyl or ethyl, particularly preferably methyl, and x is a number from 2 to 500, for example the dimethicones available under the trade names VICASIL (General Electric Company), DOW CORNING 200, DOW CORNING 225, DOW CORNING 200 (Dow Corning Corporation), and also the dimethicones available under SilCare® Silicone 41M65, SilCare® Silicone 41M70, SilCare® Silicone 41M80 (Clariant), stearyldimethylpolysiloxane, $C_{20}$-$C_{24}$-alkyldimethylpolysiloxane, $C_{24}$-$C_{28}$-alkyldimethylpolysiloxane, but also the methicones available under SilCare® Silicone 41M40, SilCare® Silicone 41M50 (Clariant), furthermore trimethylsiloxysilicates $[(CH_2)_3SiO]_{1/2]_x[SiO_2]_y}$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty-acid-, alcohol-, polyether-, epoxy-, fluorine- and/or alkyl-modified silicone compounds, and also polyether siloxane copolymers.

The compositions of the invention preferably comprise one or more surfactants.

Surfactants for the purposes of the present invention are substances which lower the surface tension of a liquid or the interfacial tension between two phases and enable or assist the formation of dispersions or emulsions. This means more particularly that the term "surfactants" in the context of the present invention also encompasses substances which are commonly termed emulsifiers.

The surfactants may be selected advantageously from the groups of the nonionic surfactants, anionic surfactants, cationic surfactants, amphoteric surfactants, and betaine surfactants.

The amount of the surfactants in the compositions of the invention (in the case of rinse-off products, for example), based on the completed compositions of the invention, is preferably from 0.01% to 50.0% by weight, more preferably from 1.0% to 30.0% by weight, with particular preference from 5.0% to 20.0% by weight, and very preferably from 5.0% to 15.0% by weight.

Preferred anionic surfactants are $(C_{10}$-$C_{22})$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic acid monoesters and diesters, fatty alcohol phosphates, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates, acyl glutamates and acyl glycinates. These compounds and mixtures thereof are used in the form of their water-soluble or water-dispersible salts, for example the sodium, potassium, magnesium, ammonium, mono-, di- and triethanolammonium, and analogous alkylammonium salts.

The amount of the anionic surfactants in the compositions of the invention is preferably from 0.1% to 30.0% by weight, more preferably from 0.2% to 20.0% by weight, and with particular preference from 0.5% to 15.0% by weight, based on the completed compositions.

Preferred cationic surfactants are quaternary ammonium salts, such as di($C_8$-$C_{22}$)-alkyldimethylammonium chloride or bromide, preferably di($C_8$-$C_{22}$)-alkyldimethylammonium chloride or bromide; ($C_8$-$C_{22}$)-alkyl-dimethylethylammonium chloride or bromide; ($C_8$-$C_{22}$)-alkyltrimethyl-ammonium chloride or bromide, preferably cetyltrimethylammonium chloride or bromide and ($C_8$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyldimethylbenzylammonium chloride, ($C_8$-$C_{22}$)-alkyl-dimethylhydroxyethylammonium chloride, phosphate, sulfate, lactate, ($C_8$-$C_{22}$)-alkylamidopropyltrimethylammonium chloride, methosulfate, N,N-bis(2-$C_8$-$C_{22}$-alkanoyloxyethyl)dimethylammonium chloride, methosulfate, N,N-bis(2-$C_8$-$C_{22}$-alkanoyloxyethyl)hydroxylethylmethyl-ammonium chloride, methosulfate.

The amount of the cationic surfactants in the compositions of the invention is preferably 0.1% to 10.0% by weight, more preferably from 0.5% to 7.0% by weight, and with particular preference from 1.0% to 5.0% by weight, based on the completed formulations.

Preferred nonionic surfactants are fatty alcohol ethoxylates (alkylpolyethylene glycols); alkylphenol polyethylene glycols; fatty amine ethoxylates (alkylaminopolyethylene glycols); fatty acid ethoxylates (acyl polyethylene glycols); polypropylene glycol ethoxylates (Pluronics®) fatty acid alkanolamides, (fatty acid amide polyethylene glycols); sucrose esters; sorbitol esters and sorbitan esters and polyglycol ethers thereof, and also $C_8$-$C_{22}$-alkyl polyglucosides.

The amount of the nonionic surfactants in the compositions of the invention (e.g. in the case of rinse-off products) is preferably in the range from 1.0% to 20.0% by weight, more preferably from 2.0% to 10.0% by weight, and with particular preference from 3.0% to 7.0% by weight, based on the completed compositions.

Furthermore, the compositions according to the invention can comprise amphoteric surfactants. These can be described as derivatives of long-chain secondary or tertiary amines which have an alkyl group with 8 to 18 carbon atoms and in which a further group is substituted by an anionic group which imparts the solubility in water, thus, for example, by a carboxyl, sulfate or sulfonate group. Preferred amphoteric surfactants are N—($C_{12}$-$C_{18}$)-alkyl-β-aminopropionates and N—($C_{12}$-$C_{18}$)-alkyl-β-imino-dipropionates as alkali metal and mono-, di- and trialkylammonium salts. Suitable further surfactants are also amine oxides. These are oxides of tertiary amines with a long-chain group having 8 to 18 carbon atoms and two mostly short-chain alkyl groups having 1 to 4 carbon atoms. Preference is given here, for example, to the $C_{10}$- to $C_{18}$-alkyldimethylamine oxides, fatty acid amidoalkyldimethylamine oxide.

A further preferred group of surfactants is betaine surfactants, also called zwitterionic surfactants. These contain in the same molecule a cationic group, in particular an ammonium group, and an anionic group, which may be a carboxylate group, sulfate group or sulfonate group. Suitable betaines are preferably alkylbetaines such as cocobetaine or fatty acid alkylamidopropylbetaines, for example cocoacylamidopropyl-dimethylbetaine or the $C_{12}$- to $C_{18}$-dimethylaminohexanoates and/or the $C_{10}$- to $C_{18}$-acylamidopropanedimethylbetaines.

The amount of the amphoteric surfactants and/or betaine surfactants in the compositions of the invention is preferably from 0.5% to 20.0% by weight and more preferably from 1.0% to 15.0% by weight, based on the completed compositions.

Preferred surfactants are lauryl sulfate, laureth sulfate, cocoamidopropylbetaine, alkylbetaines such as cocobetaine, sodium cocoyl glutamate and lauroamphoacetate.

Particularly preferred surfactants are alkylated ether sulfates having a linear or branched alkyl group with 1 to 30 carbon atoms, a linear or branched, singularly or multiply unsaturated alkenyl group having 2 to 30 carbon atoms, betaines and derivatives thereof, and particular preference is given to alkylated ether sulfates having a linear or branched alkyl group with 12 to 22 carbon atoms, betaines and their derivatives, and mixtures thereof.

In a further preferred embodiment of the invention, the compositions according to the invention additionally also comprise, as foam-boosting agents, cosurfactants from the group of alkylbetaines, alkylamidobetaines, aminopropionates, aminoglycinates, imidazolinium betaines and sulfobetaines, amine oxides, fatty acid alkanolamides and polyhydroxyamides.

The compositions according to the invention can comprise, as further auxiliaries and additives, for example waxes, emulsifiers, coemulsifiers, solubilizers, electrolytes, hydroxyl acids, stabilizers, cationic polymers, film formers, further thickeners, gelling agents, superfatting agents, refatting agents, antimicrobial active ingredients, biogenic active ingredients, astringents, deodorizing agents, sun protection filters, antioxidants, humectants, solvents, colorants, pearlizing agents, fragrances, opacifiers and/or silicones.

The compositions according to the invention can comprise waxes, for example paraffin waxes, microwaxes and ozokerites, beeswax and its component fractions, and also beeswax derivatives, waxes from the group of homopolymeric polyethylenes or copolymers of α-olefins, and natural waxes such as rice wax, candelilla wax, carnauba wax, Japan wax or shellac wax.

Emulsifiers, coemulsifiers and solubilizers which can be used are nonionic, anionic, cationic or amphoteric surface-active compounds.

Suitable nonionogenic surface-active compounds are preferably:
addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; $(C_{12}-C_{18})$-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol and in particular polyglycerol esters, such as, for example, polyglycerol polyricinoleate and polyglycerol poly-12-hydroxystearate. Ethoxylated fatty amines, fatty acid amides, fatty acid alkanolamides and mixtures of compounds of two or more of these substance classes are likewise preferably suitable.

Suitable ionogenic coemulsifiers are, for example, anionic emulsifiers, such as mono-, di- or triphosphoric acid esters, soaps (e.g. sodium stearate), fatty alcohol sulfates, but also cationic emulsifiers such as mono-, di- and trialkyl quats and polymeric derivatives thereof.

Available amphoteric emulsifiers are preferably alkylaminoalkylcarboxylic acids, betaines, sulfobetaines and imidazoline derivatives.

Fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols and cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol(19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol(14) isocetyl ether, polyethylene glycol(15) isocetyl ether, polyethylene glycol(16) isocetyl ether, polyethylene glycol(17) isocetyl ether, polyethylene glycol(18) isocetyl ether, polyethylene glycol(19) isocetyl ether, polyethylene glycol(20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolauryl ether, polyethylene glycol(13) cetylstearyl ether, polyethylene glycol(14) cetylstearyl ether, polyethylene glycol(15) cetylstearyl ether, polyethylene glycol(16) cetylstearyl ether, polyethylene glycol(17) cetylstearyl ether, polyethylene glycol(18) cetylstearyl ether, polyethylene glycol(19) cetylstearyl ether are particularly preferably used Fatty acid ethoxylates selected from the group of ethoxylated stearates, isostearates and oleates, in particular polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate are likewise preferred.

Sodium laureth-11 carboxylate can advantageously be used as ethoxylated alkylether carboxylic acid or salts thereof.

Ethoxylated triglycerides which can be used are advantageously polyethylene glycol(60) evening primrose glycerides.

It is furthermore advantageous to select the polyethylene glycol glycerol fatty acid esters from the group polyethylene glycol(20) glyceryl laurate, polyethylene glycol(6) glyceryl caprate/caprinate, polyethylene glycol(20) glyceryl oleate, polyethylene glycol(20) glyceryl isostearate and polyethylene glycol(18) glyceryl oleate/cocoate.

Among the sorbitan esters, polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate are particularly suitable.

Particularly advantageous coemulsifiers are glyceryl monostearate, glyceryl monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol(2) stearyl ether (steareth-2), alkylmethicone copolyols and alkyldimethicone copolyols, in particular cetyldimethicone copolyol, laurylmethicone copolyol.

The compositions of the invention may comprise one or more of the emulsifiers, coemulsifiers or solubilizers in amounts of 0.1% to 20.0% by weight, preferably 1.0% to 15.0% by weight and more preferably 3.0% to 10.0% by weight, based on the completed compositions.

For example electrolytes that may be used are inorganic salts, preferably ammonium or metal salts, particularly preferably of halides, for example $CaCl_2$, $MgCl_2$, LiCl, KCl, and NaCl, carbonates, hydrogencarbonates, phosphates, sulfates, nitrates, especially preferably sodium chloride, and/or organic salts, preferably ammonium or metal salts, particularly preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid.

Also included therein are aluminum salts, preferably aluminum chlorohydrate or aluminum-zirconium complex salts.

In one preferred embodiment of the invention, therefore, the compositions of the invention comprise one or more substances selected from organic and inorganic salts.

As electrolyte, the compositions according to the invention can also comprise mixtures of different salts. The content of the one or more electrolytes, based on the total composition according to the invention, is preferably from 0.01% to 20.0% by weight, more preferably from 0.1% to 10.0% by weight, and with particular preference from 0.5% to 5.0% by weight.

The polymers of the invention are acid-stable and are suitable preferably for use in cosmetic, pharmaceutical and/or dermatological compositions with a low pH of 2 to 6, more particularly for products for hair and skin cleansing and for bodycare.

The use of acidic additives and their salts makes it necessary in some cases to bring the pH of the cosmetic or dermatological compositions into a distinctly acidic range.

In a further preferred embodiment of the invention, the compositions of the invention comprise one or more hydroxy acids, more preferably one or more substances selected from alpha- and beta-hydroxy acids.

Hydroxy acids which may be present in the compositions of the invention include, preferably, lactic acid, glycolic acid, salicylic acid and alkylated salicylic acids, or citric acid. Furthermore, formulations of the invention may comprise other acidic components. Active ingredients contemplated include tartaric acid, mandelic acid, caffeic acid, pyruvic acid, oligooxamonocarboxylic and -dicarboxylic acids, fumaric acid, retinoic acid, sulfonic acids, benzoic acid, kojic acid, fruit acid, maleic acid, gluconic acid, pyruvic acid, galacturonic acid, ribonic acid, and all their derivatives, polyglycol diacids in free or partly neutralized form, vitamin C (ascorbic acid), vitamin C derivatives, dihydroxyacetone or skin-whitening actives such as arbutin or glycyrrhetic acid and salts thereof. The amount of one or more of these substances just recited, based on the total composition of the invention, is preferably from 0.1% to 20.0% by weight, more preferably from 0.2% to 10.0% by weight, and with particular preference from 0.5% to 5.0% by weight.

In a further preferred embodiment of the invention, the compositions of the invention therefore comprise one or more substances selected from vitamin C and vitamin C derivatives, the vitamin C derivatives being preferably selected from sodium ascorbyl phosphate, magnesium ascorbyl phosphate, and magnesium ascorbyl glucoside.

In another preferred embodiment of the invention, the compositions of the invention comprise one or more substances selected from benzoic acid, sorbic acid, salicylic acid, lactic acid, and para-methoxybenzoic acid. By virtue of the fact that the polymers of the invention also thicken and develop a yield point in the acidic pH range, it is possible to use the aforementioned organic acids as preservatives.

For the copolymers of the invention it is possible, as additional stabilizers, to use metal salts of fatty acids, such as magnesium stearate, aluminum stearate, and/or zinc stearate, for example, preferably in amounts of 0.1% to 10.0% by weight, more preferably from 0.5% to 8.0% by weight, and very preferably from 1.0% to 5.0% by weight, based on the completed compositions.

Suitable cationic polymers are those known under the INCI name "Polyquaternium", in particular Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and Polyquaternium 37&mineral oil&PPG trideceth (Salcare SC95), PVP-dimethylaminoethyl methacrylate copolymer, guar hydroxypropyltriammonium chloride, and calcium alginate and ammonium alginate. Furthermore, cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amidomethicones; copolymers of adipic acid and dimethylaminohydroxypropyldiethylenetriamine; polyaminopolyamide and cationic chitin derivatives, such as, for example, chitosan, can be used.

The compositions according to the invention can comprise one or more of the aforementioned cationic polymers in amounts of 0.1% to 5.0% by weight, preferably 0.2% to 3.0% by weight and particularly preferably 0.5% to 2.0% by weight, based on the completed compositions.

Furthermore, the compositions according to the invention can comprise film formers which, depending on the intended use, are selected from salts of phenylbenzimidazolesulfonic acid, water-soluble polyurethanes, for example $C_{10}$-polycarbamyl polyglyceryl ester, polyvinyl alcohol, polyvinylpyrrolidone copolymers, for example vinylpyrrolidone/vinyl acetate copolymer, water-soluble acrylic acid polymers/copolymers and esters or salts thereof, for example partial ester copolymers of acrylic acid/methacrylic acid, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate, for example available under the trade name Aristoflex® A 60 (Clariant).

The compositions according to the invention can comprise one or more film formers in amounts of from 0.1% to 10.0% by weight, preferably from 0.2% to 5.0% by weight and particularly preferably from 0.5% to 3.0% by weight, based on the completed compositions.

The desired viscosity of the compositions can be established by adding further thickeners and gelling agents. Of suitability are preferably cellulose ethers and other cellulose derivatives (e.g. carboxymethylcellulose, hydroxyethylcellulose), gelatin, starch and starch derivatives, sodium alginates, fatty acid polyethylene glycol esters, agar agar, tragacanth or dextrin derivatives, in particular dextrin esters. Furthermore, metal salts of fatty acids, preferably having 12 to 22 carbon atoms, for example sodium stearate, sodium palmitate, sodium laurate, sodium arachidates, sodium behenate, potassium stearate, potassium palmitate, sodium myristate, aluminum monostearate, hydroxyl fatty acids, for example 12-hydroxystearic acid, 16-hydroxyhexadecanoyl acid; fatty acid amides; fatty acid alkanolamides; dibenzalsorbitol and alcohol-soluble polyamides and polyacrylamides or mixtures of such are suitable. Furthermore, crosslinked and uncrosslinked polyacrylates such as carbomers, sodium polyacrylates or polymers containing sulfonic acid, such as ammonium acryloyldimethyltaurate/VP copolymer, can be used.

In a further preferred embodiment of the invention, the compositions of the invention contain 0.01% to 20.0% by weight, more preferably 0.1% to 10.0% by weight, with particular preference 0.2% to 3.0% by weight, and very preferably 0.4% to 2.0% by weight of thickeners and/or gelling agents, based on the completed compositions of the invention.

Superfatting or refatting agents which can be used are preferably lanolin and lecithin, nonethoxylated and polyethoxylated or acylated lanolin derivatives and lecithin derivatives, polyol fatty acid esters, mono-, di- and triglycerides and/or fatty acid alkanolamides, where the latter simultaneously serve as foam stabilizers, which are preferably used in amounts from 0.01% to 10.0% by weight, more preferably from 0.1% to 5.0% by weight, and with particular preference from 0.5% to 3.0% by weight based on the completed formulations of the invention.

Antimicrobial active ingredients which can be used are cetyltrimethylammonium chloride, cetylpyridinium chloride, benzethonium chloride, diisobutylethoxyethyldimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanedol, 3,4,4'-trichlorocarbanilide (triclocarban), diaminoalkylamide, for example L-lysine hexadecylamide, citrate heavy metal salts, salicylates, piroctoses, in particular zinc salts, pyrithiones and heavy metal salts thereof, in particular zinc pyrithione, zinc phenol sulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and Octopirox®, iodopropynyl butylcarbamate, methylchloroisothiazolinone, methylisothiazolinone, methyldibromoglutaronitrile, AgCl, chloroxylenol, Na salt of diethylhexyl sulfosuccinate, sodium benzoate, and phenoxyethanol, benzyl alcohol, phenoxyisopropanol, parabens, preferably butyl, ethyl, methyl and propyl paraben, and Na salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethylglycinate, hydroxyethylglycine of sorbic acid and combinations of these active substances.

The compositions of the invention comprise the active antimicrobial ingredients preferably in amounts from 0.001% to 5.0% by weight, more preferably from 0.01% to 3.0% by weight, and with particular preference from 0.1% to 2.0% by weight, based on the completed compositions of the invention.

The compositions according to the invention can furthermore comprise biogenic active ingredients selected from plant extracts, such as, for example, aloe vera, and also local anesthetics, antibiotics, antiphlogistics, antiallergics, corticosteroids, sebostatics, Bisabolol®, allantoin, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, and also vitamin E and/or derivatives thereof.

The compositions according to the invention can comprise biogenic active ingredients preferably in amounts of from 0.001% to 5% by weight, particularly preferably from 0.01% to 3.0% by weight and especially preferably from 0.1% to 2.0% by weight, based on the completed compositions.

The compositions according to the invention can comprise astringents, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc, and also aluminum chlorohydrates, preferably in amounts of from 0% to 50.0% by weight, particularly preferably in amounts of from 0.01% to 10.0% by weight and especially preferably in amounts of from 0.1% to 10.0% by weight.

Allantoin and bisabolol are preferred as deodorizing substances. They are preferably used in amounts of from 0.0001% to 10.0% by weight.

In a further preferred embodiment of the invention, the compositions of the invention comprise one or more substances selected from organic and inorganic UV filters, and with particular preference take the form of a sun protection composition.

The compositions of the invention can comprise microfine titanium dioxide, mica-titanium oxide, iron oxides, mica-iron oxide, zinc oxide, silicon oxides, ultramarine blue or chromium oxides as pigments/micropigments and also as inorganic sun protection filters or UV filters.

The inorganic sun protection or UV filters, are preferably selected from 4-aminobenzoic acid, 3-(4'-trimethylammonium)benzylideneboran-2-one methyl sulfate, camphor benzalkonium methosulfate, 3,3,5-trimethylcyclohexyl salicylate, 2-hydroxy-4-methoxybenzophenone, 2-phenylbenzimidazole-5-sulfonic acid and its potassium, sodium and triethanolamine salts, 3,3'-(1,4-phenylenedimethine)bis(7,7-dimethyl-2-oxobicyclo[2.2.1]heptane-1-methanesulfonic acid) and its salts, 1-(4-tert-butylphenyl)-3-(4-methoxyphenyl)propane-1,3-dione, 3-(4'-sulfo)benzylidenebornan-2-one and its salts, 2-ethylhexyl 2-cyano-3,3-diphenylacrylate, polymers of N-[2(and 4)-(2-oxoborn-3-ylidene-methyl)benzyl]acrylamide, 2-ethylhexyl 4-methoxycinnamate, ethoxylated ethyl 4-aminobenzoate, isoamyl 4-methoxycinnamate, 2,4,6-tris[p-(2-ethyl-hexyloxycarbonyl)anilino]-1,3,5-triazine, 2-(2H-benzotriazol-2-yl)-4-methyl-6-(2-methyl-3-(1,3,3,3-tetramethyl-1-(trimethylsilyloxy)di-siloxanyl)propyl)phenol, bis(2-ethylhexyl) 4,4'-[(6-[4-((1,1-dimethyl-ethyl)aminocarbonyl)phenylamino]-1,3,5-triazin-2,4-yl)diimino]bisbenzoate, benzophenone-3, benzophenone-4 (acid), 3-(4'-methylbenzylidene)-DL-camphor, 3-benzylidenecamphor, 2-ethylhexyl salicylate, 2-ethylhexyl 4-dimethylaminobenzoate, hydroxy-4-methoxybenzophenone-5-sulfonic acid (sulfisobenzone) and the sodium salt, 4-isopropylbenzyl salicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium and triethanolamine salts, octylmethoxycinnamic acid, isopentyl-4-methoxycinnamic acid, isoamyl-p-methoxycinnamic acid, 2,4,6-trianilino(p-carbo-2'-ethylhexyl-1'-oxy)-1,3,5-triazine (octyltriazone) phenol, 2-2(2H-benzotriazol-2-yl)-4-methyl-6-(2-methyl-3-(1,3,3,3-tetramethyl-1-(trimethylsily)oxy)disiloxanyl)propyl (drometrizoletrisiloxane) benzoic acid, 4,4-((6-(((1,1-dimethyl-ethyl)amino)carbonyl)phenyl)amino)-1,3,5-triazine-2,4-diyl)di-imino)bis,bis(2-ethylhexyl)ester)benzoic acid, 4,4-(6-(((1,1-dimethyl-ethypamino)carbonyl)phenyl) amino)-1,3,5-triazine-2,4-diyl)di-imino)bis,bis(2-ethylhexyl)ester), 3-(4'-methylbenzylidene)-DL-camphor (4-methylbenzylidenecamphor), benzylidenecamphorsulfonic acid, octocrylene, polyacrylamidomethylbenzylidenecamphor, 2-ethylhexyl salicylate (octyl salicylate), ethyl-2-hexyl 4-dimethylaminobenzoate (octyl dimethyl PABA), PEG-25 PABA, 2-hydroxy-4-methoxybenzophenone-5-sulfonic acid (benzophenone-5) and the Na salt, 2,2'-methylenebis-6-(2H-benzotriazol-2-yl)-4-(tetramethylbutyl)-1,1,3,3-phenol, sodium salt of 2-2'-bis(1,4-phenylene)-1H-benzimidazole-4,6-disulfonic acid, (1,3,5)-triazine-2,4-bis ((4-(2-ethylhexyloxy)-2-hydroxy)phenyl)-6-(4-methoxyphenyl), 2-ethylhexyl 2-cyano-3,3-diphenyl-2-propenoate, glyceryl octanoate, di-p-methoxycinnamic acid, p-aminobenzoic acid and esters thereof, 4-tert-butyl-4'-methoxydibenzoylmethane, 4-(2-β-glucopyranoxy) propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentane-dione, 2-ethylhexyl dimethoxybenzylidenedioxoimidazolidinepropionate, methylenebisbenzotriazolyl tetramethylbutylphenol, phenyl dibenzimidazoletetrasulfonate, bis-ethylhexyloxyphenol methoxyphenol triazine, tetrahydroxybenzophenones, terephthalylidenedicamphorsulfonic acid, 2,4,6-tris[4,2-ethylhexyloxycarbonyl)anilino]-1,3,5-triazine, methyl-bis (trimethylsiloxy)silylisopentyltrimethoxycinnamic acid, amyl p-dimethyl-aminobenzoate, amyl p-dimethylaminobenzoate, 2-ethylhexyl p-dimethyl-aminobenzoate, isopropyl-p-methoxycinnamic acid/diisopropylcinnamic acid esters, 2-ethylhexyl-p-methoxycinnamic acid, 2-hydroxy-4-methoxybenzophenone, 2-hydroxy-4-methoxybenzophenone-5-sulfonic acid and the trihydrate, and also 2-hydroxy-4-methoxybenzophenone-5-sulfonate sodium salt and phenylbenzimidazolesulfonic acid.

The amount of the aforementioned sun protection filters (one or more compounds) in the inventive compositions is preferably from 0.001% to 30.0% by weight, more preferably from 0.05% to 20.0% by weight, and with particular preference from 1.0% to 10.0% by weight, based on the total weight of the completed composition.

The compositions of the invention can comprise one or more antioxidants, preferably selected from amino acids (e.g. glycine, histidine, tyrosine, tryptophan) and derivatives thereof, imidazoles (e.g. urocanic acid) and derivatives thereof, peptides such as DL-carnosine, D-carnosine,L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and also salts thereof, dilauryl thiodipropionate, distearyl thiodipropionate, thiodipropionic acid and derivatives thereof (e.g. esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses, also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), superoxide dismutase and the derivatives suitable according to the invention (salts, esters, ethers, sugars, nucleotides, nucleosides, peptides and lipids) of these specified substances.

The antioxidants can protect the skin and the hair against oxidative stress. Preferred antioxidants here are vitamin E and derivatives thereof, and vitamin A and derivatives thereof.

The amount of the one or more antioxidants in the compositions of the invention is preferably from 0.001% to 30.0% by weight more preferably from 0.05% to 20.0% by weight, and with particular preference from 1.0% to 10.0% by weight, based on the total weight of the composition.

Furthermore, humectants selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxy acids, panthenol and derivatives thereof, for example D-panthenol (R-2,4-dihydroxy-N-(3-hydroxypropyl)-3,3-dimethylbutamide), DL-panthenol, calcium pantothenate, panthetine, pantotheine, panthenyl ethyl ether, isopropyl palmitate, glycerol and/or sorbitol can be used, preferably in amounts of from 0.1% to 15.0% by weight and particularly preferably from 0.5% to 5.0% by weight, based on the completed compositions.

Additionally, the compositions of the invention can comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, tert-butanol, glycerol and mixtures of said alcohols. Further preferred alcohols are polyethylene glycols with a relative molecular mass below 2000. In particular, the use of polyethylene glycol with a relative molecular mass between 200 and 600 and in amounts up to 45.0% by weight and of polyethylene glycol with a relative molecular mass between 400 and 600 in amounts of from 5.0% to 25.0% by weight is preferred. Further suitable solvents are, for example, triacetin (glycerol triacetate) and 1-methoxy-2-propanol.

The compositions of the invention may comprise one or more substances selected from colorants, examples being dyes and/or pigments. The dyes and/or pigments present in the formulations of the invention, and also organic and inorganic dyes and pigments, are selected from the corresponding positive list of the German Cosmetic Ordinance or from the EC list of cosmetic colorants.

| Chemical or other name | CIN | Color |
| --- | --- | --- |
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Cerise Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfonic acid diethylamide-1'-phenylazo)-3-hydroxy-5''-chloro-2'',4''-dimethoxy-2-naphthoic acid anilide | 12490 | red |
| Disperse Yellow 16 | 12700 | yellow |
| 1-(4-Sulfo-1-phenylazo)-4-aminobenzenesulfonic acid | 13015 | yellow |
| 2,4-Dihydroxyazobenzene-4'-sulfonic acid | 14270 | orange |
| 2-(2,4-Dimethylphenylazo-5-sulfonic acid)-1-hydroxy-naphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonic acid-4-chloro-5-carboxylic acid-1-phenylazo)-2-hydroxynaphthalene | 15525 | red |
| 1-(3-Methylphenylazo-4-sulfonic acid)-2-hydroxynaphthalene | 15580 | red |
| 1-(4',(8')-Sulfonic acid naphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxy-naphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo)-1,3-dihydroxy-benzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |

-continued

| Chemical or other name | CIN | Color |
| --- | --- | --- |
| Acid Red 73 | 27290 | red |
| 2-[4''-(4''-Sulfo-1'''-phenylazo)-7'-sulfo-1'-naphthylazo]-1-hydroxy-7-aminonaphthalene-3,6-disulfonic acid | 27755 | black |
| 4'-[(4''-Sulfo-1'''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-Carotenealdehyde ($C_{30}$) | 40820 | orange |
| trans-Apo-8'-Carotenic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenyl-carbinol | 42051 | blue |
| 4-[(4-N-Ethyl-p-sulfobenzylamino)phenyl-(4-hydroxy-2-sulfophenyl)(methylene)-1-(N-ethyl-N-p-sulfobenzyl)-2,5-cyclohexadieneimine] | 42053 | green |
| Acid Blue 7 | 42080 | blue |
| (N-Ethyl-p-sulfobenzylaminophenyl)-(2-sulfophenyl)-methylene-(N-ethyl-N-p-sulfobenzyl)cyclohexadieneimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4''-(N-diethyl)-amino-2-methyl-N-ethyl-N-m-sulfobenzylfuchsonimmonium | 42735 | blue |
| 4'-(N-Dimethyl)amino-4''-(N-phenyl)aminonaphtho-N-dimethylfuchsonimmonium | 44045 | blue |
| 2-Hydroxy-3,6-disulfo-4,4'-bisdimethylaminonaphtho-fuchsinimmonium | 44090 | green |
| Acid red | 45100 | red |
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidine)anthraquinone | 61570 | green |
| Acid Blue 80 | 61585 | blue |
| Acid Blue 62 | 62045 | blue |
| N,N'-Dihydro-1,2,1',2'-anthraquinoneazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha, beta- or gamma-Carotene | 75130 | orange |
| Keto and/or hydroxyl derivatives of carotene | 75135 | yellow |
| Guanine or pearlescent agents | 75170 | white |
| 1,7-Bis(4-hydroxy-3-methoxyphenyl)-1,6-heptadiene-3,5-dione | 75300 | yellow |

-continued

| Chemical or other name | CIN | Color |
|---|---|---|
| Complex salt (Na,Al,Ca) of carminic acid | 75470 | red |
| Chlorophyll a and b; copper compounds of the chlorophylls and chlorophyllines | 75810 | green |
| Aluminum | 77000 | white |
| Aluminum hydrate | 77002 | white |
| Water-containing aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromic oxide | 77288 | green |
| Chromium oxide, hydrated | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxides and hydroxides | 77491 | red |
| Hydrated iron oxide | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot {}^7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Caramel | | brown |
| Capsanthin, Capsorubin | | orange |
| Betanine | | red |
| Benzopyrilium salts, anthocyanines | | red |
| Aluminum, zinc, magnesium and calcium stearate | | white |
| Bromothymol Blue | | blue |
| Bromocresol Green | | green |
| Acid Red 195 | | red |

Also advantageous are oil-soluble natural dyes, such as, for example, paprika extracts, β-carotene and cochineal.

Pearlescent pigments are also advantageously used, e.g. pearl essence (guanine/hypoxanthine mixed crystals from fish scales) and mother-of-pearl (ground mussel shells), monocrystalline pearlescent pigments, such as, for example, bismuth oxychloride (BiOCl), layer-substrate pigments, e.g. mica/metal oxide, silver-white pearlescent pigments of $TiO_2$, interference pigments ($TiO_2$, varying layer thickness), color luster pigments ($Fe_2O_3$) and combination pigments ($TiO_2/Fe_2O_3$, $TiO_2/Cr_2O_3$, $TiO_2$/Prussian blue, $TiO_2$/carmine).

Within the context of the present invention, effect pigments are to be understood as meaning pigments which bring about particular optical effects as a result of their refractive properties. Effect pigments impart luster or glitter effects to the treated surface (skin, hair, mucosa) or are able to optically conceal skin unevenness and skin wrinkles through diffuse light scattering. As a particular embodiment of the effect pigments, interference pigments are preferred. Particularly suitable effect pigments are for example, mica particles which are coated with at least one metal oxide. Besides mica, a sheet silicate, silica gel and other $SiO_2$ modifications are also suitable as carriers. A metal oxide which is often used for the coating is, for example, titanium oxide, to which, if desired, iron oxide can be admixed. The reflection properties can be influenced via the size and the shape (e.g. spherical, ellipsoidal, flattened, planar, nonplanar) of the pigment particles and also via the thickness of the oxide coating. Other metal oxides too, e.g. bismuth oxychloride (BiOCl), and the oxides of, for example, titanium, in particular the $TiO_2$ modifications anatase and rutile, and of aluminum, tantalum, niobium, zirconium and hafnium. With magnesium fluoride ($MgF_2$) and calcium fluoride (fluorspar, $CaF_2$), too, it is possible to produce effect pigments.

The effects can be controlled not only via the particle size but also via the particle size distribution of the pigment collective. Suitable particle size distributions range, for example, from 2-50 µm, 5-25 µm, 5-40 µm, 5-60 µm, 5-95 µm, 5-100 µm, 10-60 µm, 10-100 µm, 10-125 µm, 20-100 µm, 20-150 µm, and <15 µm. A broader particle size distribution, for example of 20-150 µm, brings about glittering effects, whereas a narrower particle size distribution of <15 µm provides a uniform satin appearance.

The compositions of the invention comprise effect pigments preferably in amounts of from 0.1% to 20.0% by weight, particularly preferably from 0.5% to 10.0% by weight and especially preferably from 1.0% to 5.0% by weight, in each case based on the total weight of the compositions.

Preferably suitable as pearlizing component are fatty acid monoalkanolamides, fatty acid dialkanolamides, monoesters or diesters of alkylene glycols, in particular ethylene glycol and/or propylene glycol or oligomers thereof, with higher fatty acids, such as, for example, palmitic acid, stearic acid and behenic acid, monoesters or polyesters of glycerol with carboxylic acids, fatty acids and metal salts thereof, ketosulfones or mixtures of the specified compounds.

Particular preference is given to ethylene glycol distearates and/or polyethylene glycol distearates having on average 3 glycol units.

Where the compositions of the invention comprise pearlizing compounds, these are preferably present in the compositions of the invention in an amount of from 0.1% to 15.0% by weight and particularly preferably in an amount of from 1% to 10.0% by weight.

Fragrance and/or perfume oils which may be used are individual odorant compounds, e.g. the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ethers, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, alpha-isomethylionone and methyl cedryl ketone, the alcohols include anethol, citronellol, eugenol, geraniol, linalool, phenylethyl alcohol and terpineol, and the hydrocarbons include primarily the terpenes and balsams. Preference is given to using mixtures of different odorants which together produce a pleasing scent note.

Perfume oils can also comprise natural odorant mixtures, as are accessible from vegetable or animal sources, e.g. pine oil, citrus oil, jasmine oil, lily oil, rose oil or ylang-ylang oil. Essential oils of relatively low volatility, which in most cases are used as aromatic components, are also suitable as perfume oils, e.g. sage oil, chamomile oil, clove oil, melissa oil, mint oil, cinnamon leaf oil, linden blossom oil, juniperberry oil, vetiver oil, olibanum oil, galbanum oil and ladanum oil.

As opacifiers it is possible to use polymer dispersions, more particularly polyacrylate derivative dispersions, polyacrylamide derivative dispersions, poly(acrylate derivative-co-acryalmide derivative) dispersions, poly(styrene derivatives-co-acrylate derivative) dispersions, saturated and unsaturated fatty alcohols.

As silicone it is possible to use the substances identified above among the silicone oils and silicone waxes.

As acids or alkalis for pH adjustment it is possible with preference to use mineral acids, more particularly HCl, inorganic bases, especially NaOH or KOH, and organic acids, especially citric acid.

The compositions of the invention have pH values of preferably 2 to 10, more preferably from 2 to 7, and with particular preference from 2.5 to 6.5.

In a further preferred embodiment of the invention, the compositions of the invention are in the form of shower gels or shampoos.

The polymers of the invention are suitable advantageously as thickeners, consistency modifiers, emulsifiers, sensorial additives, solubilizers, dispersants, lubricants, adherents, stabilizers or yield point formers.

The invention accordingly further provides the use of one or more of the polymers of the invention as thickener, consistency modifier, emulsifier, sensorial additive, solubilizer, dispersant, lubricant, adherent, stabilizer or yield point former, preferably as thickener, consistency modifier or yield point former, more preferably as thickener or yield point former, and with more particular preference as yield point former, very preferably in cosmetic, dermatological or pharmaceutical compositions.

The polymers of the invention are suitable with particular preference as thickener, consistency modifier, emulsifier, sensorial additive, solubilizer, dispersant, lubricant, adherent, stabilizer or yield point former, preferably as thickener, consistency modifier or yield point former, or more preferably as thickener or yield point former, and with more particular preference as yield point former, in liquid compositions, preferably in liquid cosmetic, dermatological or pharmaceutical compositions, with a high fraction of one or more surfactants.

One particularly preferred embodiment of the invention, therefore, is the use of one or more of the polymers of the invention as thickener, consistency modifier, emulsifier, sensorial additive, solubilizer, dispersant, lubricant, adherent, stabilizer or yield point former, preferably as thickener, consistency modifier or yield point former, or more preferably as thickener or yield point former, and with more particular preference as yield point former, in liquid compositions having a surfactant fraction of 0.01% to 50.0% by weight, preferably of 1.0% to 30.0% by weight, more preferably of 5.0% to 20.0% by weight, and with particular preference of 5.0% to 15.0% by weight, very preferably in cosmetic, dermatological or pharmaceutical compositions.

In a further particularly preferred embodiment of the invention, the polymers of the invention are used as thickeners or yield point formers, preferably as yield point formers, for stabilizing organic or inorganic particles, oil droplets or gas bubbles, more preferably in cosmetic, dermatological or pharmaceutical compositions.

In another particularly preferred embodiment of the invention, the polymers of the invention are used as thickeners or yield point formers, preferably as yield point formers, for stabilizing organic or inorganic particles, oil droplets or gas bubbles in compositions with an aqueous, aqueous-alcoholic, aqueous, surfactant-containing or aqueous-alcoholic, surfactant-containing basis, preferably in corresponding cosmetic, dermatological or pharmaceutical compositions.

In a further particularly preferred embodiment of the invention, the polymers of the invention are used as thickeners or yield point formers, preferably as yield point formers, in liquid compositions comprising one or more surfactants for stabilizing organic or inorganic particles, oil droplets or gas bubbles, preferably in liquid cosmetic, dermatological or pharmaceutical compositions.

In an especially preferred embodiment of the invention, the polymers of the invention are used as thickeners or yield point formers, preferably as yield point formers, for stabilizing organic or inorganic particles, oil droplets or gas bubbles in compositions with high surfactant concentrations, preferably from 5.0% to 20.0% by weight and more preferably from 5.0% to 15.0% by weight. The compositions are preferably cosmetic, dermatological or pharmaceutical compositions. Compositions of this kind are preferably in the form of clear solutions.

In a further preferred embodiment of the invention, the polymers of the invention are used for stabilizing emulsions, preferably salt-containing emulsions, more preferably salt-containing cosmetic, dermatological or pharmaceutical emulsions.

The polymers of the invention are acid-stable and are suitable advantageously for use in cosmetic, dermatological or pharmaceutical compositions with a low pH, more particularly for the care and treatment of the skin of the body or face.

The present invention therefore further provides for the use of one or more polymers of the invention for the care and treatment of the skin of the body or face, preferably in cosmetic, dermatological or pharmaceutical compositions, more preferably in acidic cosmetic, dermatoogical or pharmaceutical compositions.

The uses according to the invention preferably take place in cosmetic, pharmaceutical or dermatological compositions.

It is further advantageous that the polymers of the invention can be used, even without accompanying use of an additional yield point former and/or without accompanying use of additional thickener, in compositions, preferably in cosmetic, dermatological or pharmaceutical compositions. The accompanying use of additional yield point formers and/or thickeners is therefore not mandatory, though is possible. Combination with other known yield point formers and/or thickeners may be desirable in order to bring about specific cosmetic profiles and for the exploitation of synergistic effects.

It is further advantageous that the polymers of the invention, even without accompanying use of an additional yield point former and/or thickener, can be used in aqueous, aqueous-alcoholic, aqueous, surfactant-containing, aqueous-alcoholic, surfactant-containing compositions, preferably in corresponding cosmetic, dermatological or pharmaceutical compositions. In one particularly preferred embodiment of the invention, therefore, the compositions of the invention are present in the form of aqueous, surfactant-containing or aqueous-alcoholic, surfactant-containing compositions without addition of an additional yield point former and/or of an additional thickener.

The polymers of the invention which comprise structural units of the formula (2) in which n is greater than 1 are notable, for example, in that when used in corresponding compositions, more particularly in corresponding cosmetic, pharmaceutical or dermatological compositions, even over a wide pH range and more particularly at pH levels of 2 to 10, they form particularly advantageous yield points and produce particularly clear compositions.

The examples and applications below are intended to illustrate the invention in more detail without, however, limiting it thereto.

EXAMPLES

The examples and applications below are intended to illustrate the invention in more detail without, however, limiting it thereto.

1. Polymerization

General polymerization procedure for preparing the polymers of the invention by the precipitation process in tert-butanol A 1 liter Quickfit flask with reflux condenser, gas inlet, internal thermometer, and stirrer is charged with 400 g of tert-butanol, which is admixed with the calculated amount of 2-acrylamido-2-methyl-1-propanesulfonic acid (AMPS®, Lubrizol). Then neutralization is carried out by introduction of $NH_3$ (target pH 6-7) and the calculated amount of 2-carboxyethyl acrylate (Sigma-Aldrich) or 2-carboxyethyl acrylate oligomer mixture (Bimax Chemicals Ltd) and the calculated amount of crosslinker are added to the reaction mixture. If further comonomers should be required, they can be added after the neutralization of the acrylamido-2-methyl-1-propanesulfonic acid (AMPS®, Lubrizol). Should the pH of the reaction mixture have drifted into the acidic range following the addition of comonomer, neutralization is repeated by introduction of $NH_3$ (target pH 6-7). After the mixture has been rendered inert using $N_2$ or argon, dimethyl 2,2'-aobisisobutyrate (V-601) initiator is added, at an internal temperature of 60° C., and the polymerization reaction is initiated. After a few minutes, the completed polymer is precipitated. The mixture is heated at reflux for two hours and the polymer is then freed from the solvent on a suction filter and dried under reduced pressure. This procedure can be applied generally to all polymerization reactions described below.

The 2-carboxyethyl acrylate oligomer mixture that is used, from Bimax Chemicals Ltd., is composed of 10-20% by weight acrylic acid, 30-60% by weight 2-carboxyethyl acrylate, and 30-60% by weight higher oligomers of 2-carboxyethyl acrylate.

2. Example 1

Polymerization was carried out in accordance with the general polymerization procedure in section 1).

| Reactant | g | mol % |
|---|---|---|
| Acrylamido-2-methyl-1-propanesulfonic acid | 90 | 89.5 |
| 2-Carboxyethyl acrylate oligomer mixture | 8.25 | 10.0 |
| Glycerol propoxylate triacrylate (GPTA) | 0.58 | 0.5 |
| Dimethyl 2,2'-azobisisobutyrate (V-601)* | 1.1 | — |

*based on the monomer concentration used

3. Example 2

Polymerization was carried out in accordance with the general polymerization procedure in section 1).

| Reactant | g | mol % |
|---|---|---|
| Acrylamido-2-methyl-1-propanesulfonic acid | 90 | 89.25 |
| 2-Carboxyethyl acrylate oligomer mixture | 8.25 | 10.0 |
| Glycerol propoxylate triacrylate (GPTA) | 0.88 | 0.75 |
| Dimethyl 2,2'-azobisisobutyrate (V-601)* | 1.1 | — |

*based on the monomer concentration used

4. Example 3

Polymerization was carried out in accordance with the general polymerization procedure in section 1).

| Reactant | g | mol % |
|---|---|---|
| Acrylamido-2-methyl-1-propanesulfonic acid | 90.0 | 87.5 |
| 2-Carboxyethyl acrylate oligomer mixture | 8.4 | 12 |
| Pentaerythritol diacrylate monostearate (PEAS) | 1.26 | 0.5 |
| Dimethyl 2,2'-azobisisobutyrate (V-601)* | 1.1 | — |

*based on the monomer concentration used

5. Example 4

Polymerization was carried out in accordance with the general polymerization procedure in section 1).

| Reactant | g | mol % |
|---|---|---|
| Acrylamido-2-methyl-1-propanesulfonic acid | 90 | 85.5 |
| 2-Carboxyethyl acrylate oligomer mixture | 8.6 | 10.0 |
| Dimethylacryamide (DMAAm) | 2.0 | 4.0 |
| Pentaerythritol diacrylate monostearate (PEAS) | 1.29 | 0.5 |
| Dimethyl 2,2'-azobisisobutyrate (V-601)* | 1.2 | — |

*based on the monomer concentration used

6. Example 5

Polymerization was carried out in accordance with the general polymerization procedure in section 1).

| Reactant | g | mol % |
|---|---|---|
| Acrylamido-2-methyl-1-propanesulfonic acid | 90 | 79.5 |
| 2-Carboxyethyl acrylate oligomer mixture | 9.3 | 10.0 |
| Dimethylacryamide (DMAAm) | 5.4 | 10.0 |
| Pentaerythritol diacrylate monostearate (PEAS) | 1.36 | 0.5 |
| Dimethyl 2,2'-azobisisobutyrate (V-601)* | 1.3 | — |

*based on the monomer concentration used

7. Example 6

Polymerization was carried out in accordance with the general polymerization procedure in section 1).

| Reactant | g | mol % |
|---|---|---|
| Acrylamido-2-methyl-1-propanesulfonic acid | 71.0 | 44.5 |
| 2-Carboxyethyl acrylate | 17.0 | 15 |
| Dimethylacryamide (DMAAm) | 30.5 | 40 |
| Trimethylolpropane triacrylate (TMPTA) | 1.2 | 0.5 |
| Dilauryl peroxide (DLP) | 1.7 | — |

* based on the monomer concentration used

8. Example 7

Polymerization was carried out in accordance with the general polymerization procedure in section 1).

| Reactant | g | mol % |
|---|---|---|
| Acrylamido-2-methyl-1-propanesulfonic acid | 90 | 86.5 |
| 2-Carboxyethyl acrylate | 10.25 | 12.0 |
| Dimethylacryamide (DMAAm) | 0.5 | 1.0 |
| Diethylene glycol dimethacrylate (DEGDMA) | 0.61 | 0.5 |
| Dimethyl 2,2'-azobisisobutyrate (V-601)* | 1.20 | — |

*based on the monomer concentration used

9. Example 8

Polymerization was carried out in accordance with the general polymerization procedure in section 1).

| Reactant | g | mol % |
|---|---|---|
| Acrylamido-2-methyl-1-propanesulfonic acid | 90.0 | 88.0 |
| 2-Carboxyethyl acrylate | 7.0 | 9.7 |
| n-Butyl acrylate | 1.3 | 2.0 |
| Glycerol 1,3-diglycerolate diacrylate (GDDA) | 0.51 | 0.3 |
| Dimethyl 2,2'-azobisisobutyrate (V-601)* | 1.1 | — |

*based on the monomer concentration used

10. Example 9

Polymerization was carried out in accordance with the general polymerization procedure in section 1).

| Reactant | g | mol % |
|---|---|---|
| Acrylamido-2-methyl-1-propanesulfonic acid | 90.0 | 86.8 |
| 2-Carboxyethyl acrylate | 7.0 | 9.6 |
| Dimethylacryamide (DMAAm) | 1.0 | 2.0 |
| 1,6-Hexanediol dimethacrylate (HDDMA) | 1.91 | 1.6 |
| Dimethyl 2,2'-azobisisobutyrate (V-601)* | 1.11 | — |

*based on the monomer concentration used

11. Example 10

Polymerization was carried out in accordance with the general polymerization procedure in section 1).

| Reactant | g | mol % |
|---|---|---|
| Acrylamido-2-methyl-1-propanesulfonic acid | 90.0 | 87.7 |
| 2-Carboxyethyl acrylate | 7.0 | 9.8 |
| Poly(ethylene glycol) monoacrylate | 3.8 | 2.0 |
| Glycerol propoxylate triacrylate (GPTA) | 0.59 | 0.5 |
| Dimethyl 2,2'-azobisisobutyrate (V-601)* | 1.10 | — |

*based on the monomer concentration used

The 2-carboxyethyl acrylate oligomer mixture used, from Bimax Chemicals Ltd., can be purified by chromatographic methods. For example, the acrylic acid can be removed and the resulting oligomer mixture can be used, for example, in examples 1 to 5 set out above.

B) Examples relating to cosmetic compositions comprising polymers of the invention:

All of the percentage figures below are in weight percent (% by weight), unless explicitly indicated otherwise.

The following cosmetic formulations were prepared with copolymers of the invention:

Example A

Anti-Aging Cream Gel

| | | |
|---|---|---|
| A | Genapol ® DAT | 2.00% |
| | PEG-150 Polyglyceryl-2 tristearate and PEG-6 caprylic/capric glyceride | |
| B | Water | ad 100% |
| C | Mineral oil | 5.00% |
| | SilCare ® Silicone 31M50 | 3.00% |
| | Caprylyl trimethicone | |

-continued

| | | |
|---|---|---|
| D | Polymer of example 4 | 1.80% |
| E | Glycolic acid 30%* | 6.00% |
| | Phenonip ® | 0.50% |
| | Phenoxyethanol (and) methylparaben (and) ethylparaben (and) butylparaben (and) propylparaben (and) isobutylparaben | |
| F | Genapol ® LA 070 | 3.00% |
| | Laureth-7 | |

Preparation
I Dissolve A in B with stirring and gentle heating
II Stir D into C
III I to II and stir until a homogeneous gel is obtained
IV Add E to III
V Add F to IV and stir together

Example B

O/W Sun Protection Cream

| | | |
|---|---|---|
| A | Hostaphat ® CS 120 | 5.00% |
| | Stearyl phosphate | |
| | Tegin ® M | 2.50% |
| | Glyceryl stearate | |
| | Stearic acid | 2.00% |
| | Cetyl alcohol | 1.00% |
| | Abil ® 100 | 2.00% |
| | Dimethicone | |
| | Mineral oil, low viscosity | 3.00% |
| | Cetiol ® 868 | 3.00% |
| | Ethylhexyl stearate | |
| | Velsan ® CCT | 3.00% |
| | Caprylic/capric triglyceride | |
| | UV-Titan M210 | 5.00% |
| | Ultrafine titanium dioxide | |
| B | Polymer of example 5 | 0.20% |
| C | Hostapon ® CLG | 0.60% |
| | Sodium lauroyl glutamate | |
| | Eusolex ® 232 | 4.00% |
| | Phenylbenzimidazole sulfonic acid | |
| | Tris(hydroxymethyl) aminomethane | q.s. |
| | Trometamine | |
| | Allantoin | 0.20% |
| | Glycerol | 5.00% |
| | Preservative | q.s. |
| | Water | ad 100% |
| D | Fragrance | 0.30% |

Preparation
I Melt A at 80° C., then add component B
II Homogenize I
III Heat C to 80° C.
IV Stir III into II
V Stir IV until cooling
VI Add D to V at 35° C.
VII Homogenize emulsion

Example C

Shampoo with Pearlizer

| | | |
|---|---|---|
| A | Water | ad 100% |
| B | Polymer of example 2 | 2.50% |
| C | Genapol ® LRO liq. | 38.50% |
| | Sodium laureth sulfate | |
| | Genagen ® CAB | 15.00% |
| | Cocamidopropyl betaine | |
| | Hostapon ® KCG | 8.30% |
| | Sodium cocoyl glutamate | |

-continued

| | | |
|---|---|---|
| D | Genapol ® TSM | 4.00% |
| | Na benzoate | 0.40% |

Preparation
I Mix B with A until a homogeneous gel is obtained
II Add components of C and stir until fully dissolved
III Add components of D to II
IV Adjust pH to pH = 4.5.

Example D

Suncream with Zinc Oxide

| | | |
|---|---|---|
| A | Hostaphat ® KL 340 D | 1.00% |
| | Trilaureth-4 phosphate | |
| | Mineral oil, low viscosity | 8.00% |
| | Isopropyl palmitate | |
| | Velsan ® CCT | 2.00% |
| | Caprylic/capric triglyceride | |
| | Glyceryl stearate | 0.50% |
| | Cetearyl alcohol | 0.50% |
| B | Polymer of example 4 | 0.80% |
| C | Glycerol | 5.00% |
| | Alcohol | 1.00% |
| | Water | ad 100% |
| D | Tocopheryl acetate | 1.00% |
| | Z-Cote HP1 | 10.00% |
| | Zinc oxide and dimethicone | |
| | Preservative | q.s. |
| E | Fragrance | 0.30% |

Preparation
I Melt A at 70° C., then add B
II Heat C to 40° C.
III Stir II into I
IV Stir D at 35° C. into III
V Add E to IV

Example E

Cream Gel with Water-Soluble Sun Protection

| | | |
|---|---|---|
| A | Eusolex ® 232 | 2.00% |
| | Phenylbenzimidazole sulfonic acid | |
| B | Water | ad 100% |
| C | Polymer of example 4 | 2.10% |
| D | Tegosoft TN | 5.00% |
| | C12-15 Alkylbenzoate | |
| | SilCare ® silicone 31M50 | 3.00% |
| | Caprylyl trimethicone | |
| E | Nipaguard ® MPA | q.s. |
| | Benzyl alcohol (and) methylparaben (and) Propylparaben | |
| | Genapol ® LA 070 | 2.50% |
| | Laureth-7 | |
| | Fragrance | q.s. |

Preparation
I Mix A with B and neutralize to approximately pH 7.3
II Add C and stir until a homogeneous gel is obtained
III Mix components of D and add to II
IV Add E to III

Example F

Whitening Gel

| | | |
|---|---|---|
| A | Genapol ® T 250 | 2.00% |
| | Ceteareth-25 | |
| | Genapol ® DAT 100 | 1.10% |
| | PEG-150 polyglyceryl-2 tristearate | |
| B | Water | ad 100.00% |
| C | Ascorbic acid 2-glucoside | 3.00% |
| | Nipaguard ® DMDMH | q.s. |
| | DMDM Hydantoin | |
| D | Polymer of example 4 | 3.00% |
| E | Sodium hydroxide | q.s. |

Preparation
I Dissolve components A in B with stirring and gentle heating
II Stir until cooling (25° C.) and add C
III Add D and stir until a homogeneous gel is obtained
IV Set a pH of 6 with E

Example G

Antidandruff Shampoo

| | | |
|---|---|---|
| A | Water | ad 100% |
| B | Polymer of example 1 | 2.50% |
| C | Genapol ® LRO liq. | 38.50% |
| | Sodium laureth sulfate | |
| | Genagen ® CAB | 15.00% |
| | Cocamidopropyl betaine | |
| | Hostapon ® KCG | 8.30% |
| | Sodium cocoyl glutamate | |
| D | Zinc pyrithion | 1.80% |
| | Preservative | q.s. |

Preparation
I Mix B with A and stir until a homogeneous gel is obtained
II Add components C and stir until completely dissolved
III Add components of D to II

Example H

Shower Gel with Optical Effect (1)

| | | |
|---|---|---|
| A | Genapol ® LRO liq. | 49.95% |
| | Sodium laureth sulfate | |
| | Genagen ® CAB | 5.00% |
| | Cocamidopropylbetaine | |
| B | Water | ad 100% |
| C | Polymer of example 2 | 1.50% |
| D | Na sorbate | 0.40% |
| E | Citric acid | q.s. |
| | Cirebelle 104 | 0.20% |

Preparation
I Mix A with B
II When dissolved, add C to I and stir until a homogeneous solution is formed
III Add D to II
IV Set pH to 5.0 with E

Example I

Shower Gel of Optical Effect (2)

| | | |
|---|---|---|
| A | Genapol ® LRO liquid | 30.00% |
| | Sodium laureth sulfate | |
| | Hostapon ® KCG | 5.00% |
| | Sodium cocoyl glutamate | |
| | Velsan ® CG 070 | 2.00% |
| | PEG-7 glyceryl cocoate | |
| | Genagen ® CAB | 6.00% |
| | Cocamidopropyl betaine | |
| | Genapol ® LA 030 | 2.00% |
| | Laureth-3 | |
| B | Water | ad 100% |
| C | Polymer of example 3 | 1.50% |
| D | Na sorbate | 0.30% |

Preparation
I Mix A with B until the components are fully dissolved
II Add C to I; stir until a homogeneous solution is formed
III Add D to II The air bubbles included in the course of stirring are stably dispersed by the polymer of the invention.

The invention claimed is:
1. A water-soluble or water-swellable polymer comprising
   a) 20.0 to 98.99 mol % of at least one independent repeating structural unit of the formula (1)

$$-[CH_2-CR^1]-\underset{H}{\overset{O}{\underset{\|}{C}}}-N-A-\underset{O}{\overset{O}{\underset{\|}{S}}}-O^- Q^+ \quad (1)$$

wherein
   $R^1$ is hydrogen, methyl or ethyl,
   A is a linear $C_1$-$C_{12}$ alkylene or a branched $C_1$-$C_{12}$ alkylene, and
   $Q^+$ is $H^+$, $NH_4^+$, an organic ammonium ion $[NHR^5R^6R^7]^+$, $Li^+$, $Na^+$, $K^+$, ½ $Ca^{++}$, ½ $Mg^{++}$, ½ $Zn^{++}$, ⅓ $Al^{+++}$, or is a mixture of these ions,
      wherein $R^5$, $R^6$, and $R^7$, independently of one another, are hydrogen, a linear alkyl group having 1 to 22 carbon atoms, a branched alkyl group having 1 to 22 carbon atoms, a linear and singularly unsaturated alkenyl group having 2 to 22 carbon atoms, a linear and multiply unsaturated alkenyl group having 2 to 22 carbon atoms, a branched and singularly unsaturated alkenyl group having 2 to 22 carbon atoms, a branched and multiply unsaturated alkenyl group having 2 to 22 carbon atoms, a $C_6$-$C_{22}$ alkylamidopropyl group, a linear monohydroxyalkyl group having 2 to 10 carbon atoms, a linear di-hydroxyalkyl group having 3 to 10 carbon atoms, or a branched di-hydroxyalkyl group having 3 to 10 carbon atoms, and wherein at least one of the radicals $R^5$, $R^6$, and $R^7$ is not hydrogen and
   b) 1.0 to 79.99 mol % of at least one independent repeating structural unit of the formula (2)

$$-[\underset{H_2}{C}-CR^{1a}]-\underset{O}{\overset{O}{\underset{\|}{C}}}-[O-B]_n-O^- X^+ \quad (2)$$

wherein
  $R^{1a}$ is hydrogen, methyl or ethyl,
  $X^+$ is $H^+$, $NH_4^+$ an organic ammonium ion $[NHR^5R^6R^7]^+$, $Li^+$, $Na^+$, $K^+$, ½ $Ca^{++}$, ½ $Mg^{++}$, ½ $Zn^{++}$, ⅓ $Al^{+++}$, or is a mixture of these ions,
    wherein $R^5$, $R^6$, and $R^7$, independently of one another, are hydrogen, a linear alkyl group having 1 to 22 carbon atoms, a branched alkyl group having 1 to 22 carbon atoms, a linear and singularly unsaturated alkenyl group having 2 to 22 carbon atoms, a linear and multiply unsaturated alkenyl group having 2 to 22 carbon atoms, a branched and singularly unsaturated alkenyl group having 2 to 22 carbon atoms, a branched and multiply unsaturated alkenyl group having 2 to 22 carbon atoms, a $C_6$-$C_{22}$ alkylamidopropyl group, a linear monohydroxyalkyl group having 2 to 10 carbon atoms, a linear di-hydroxyalkyl group having 3 to 10 carbon atoms, or a branched di-hydroxyalkyl group having 3 to 10 carbon atoms, and wherein at least one of the radicals $R^5$, $R^6$, and $R^7$ is not hydrogen,
  B is a linear alkylene group having 1 to 6 carbon atoms or a branched alkylene group having 1 to 6 carbon atoms, and
  n is an integer from 1 to 10,
  and
  c) 0.01 to 8.0 mol %, of at least one crosslinking structural unit, wherein the at least one crosslinking structural unit is glycerol propoxylate triacrylate (GPTA),
  wherein mol % is based on the total number of moles of monomers in the polymer, and where the degree of neutralization of the at least one structural unit of the formula (1) is from 50.0 to 100 mol %, wherein the degree of neutralization is the ratio of moles of neutralized units of formula (1) to the total number of moles of units of formula (1).

2. The water-soluble or water-swellable polymer as claimed in claim 1, wherein the at least one structural unit of the formula (1) is derived from 2-acrylamido-2-methyl-propanesulfonic acid.

3. The water-soluble or water-swellable polymer as claimed in claim 1, wherein the fraction of the at least one structural unit of the formula (2) in which n is an integer of two to ten within component b) is from 10.0 mol % to 79.99 mol %.

4. The water-soluble or water-swellable polymer as claimed in claim 1, wherein the at least one structural unit of the formula (2), B is the group —$CH_2CH_2$— and n is an integer from 1 to 5.

5. The water-soluble or water-swellable polymer as claimed in claim 1, wherein the counterion $Q^+$ in the at least one structural unit of the formula (1) is selected from the group consisting of $NH_4^+Li^+$, $Na^+$, $Ca^{++}Mg^{++}$ and mixtures of these ions, and the counterion $X^+$ in the at least one structural unit in the formula (2) is selected from the group consisting of $H^+$, $NH_4^+Li^+$, $Na^+$, $Ca^{++}Mg^{++}$, and mixtures of these ions.

6. The water-soluble or water-swellable polymer as claimed in claim 1, comprising
  a) 50.0 to 96.99 mol % of the at least one structural unit of the formula (1),
  b) 3.0 to 49.99 mol % of the at least one structural unit of the formula (2), and
  c) 0.01 to 5.0 mol % of the at least one crosslinking structural unit of component c), wherein mol % is based on the total number of moles of monomers in the polymer.

7. The water-soluble or water-swellable polymer of claim 1, comprising
  ab) 29.99 to 98.99 mol %, of a mixture of the at least one independent repeating structural unit of formula (1) and the at least one independent repeating structural unit of formula (2) of the formulae (1) and (2),
  c) 0.01 to 8.0 mol % of the at least one crosslinking structural unit of component c), and further comprising
  d) 0.01 to 70.0 mol % of at least one independent repeating noncrosslinking structural unit obtained from at least one compound of the formula (4)

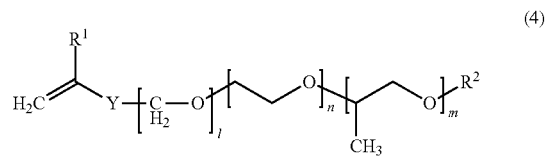

wherein
  $R^1$ is hydrogen, methyl or ethyl,
  $R^2$ is H, a linear alkyl group having 1 to 50 carbon atoms, a branched alkyl group having 1 to 50 carbon atoms, a linear monohydroxyalkyl group having 2 to 6 carbon atoms, a branched monohydroxyalkyl group having 2 to 6 carbon atoms, a linear dihydroxyalkyl group having 2 to 6 carbon atoms, a branched dihydroxyalkyl group having 2 to 6 carbon atoms, —(CO—O—$R^7$—)$_o$ $R^8$, or —(CO—$NR^5$—$R^7$—)$_p R^8$,
  l, m, n, o, and p, each independently, are an integer from 0 to 300,
  Y is a chemical bond, O, $NR^3$, S, $PR^3$, $CH_2$, $CH_2O$, $CH_2NR^3$, $CH_2S$, C(O), —C(O)O, OC(O), C(O)$NR^3$, $NR^3$C(O), C($NR^4$)$NR^3$, C(O)S, $R^6$OC(O)O, $R^6$OC(O)$NR^3$, $R^6$OC(O)S, $R^6$P(O)O, $R^6$OP(O)O, $R^6$S(O), $R^6$S(O)(O), $R^6$S(O)O, $R^6$S(O)(O)O, $R^6$OS(O)O or $R^6$OS(O)(O)O,
  $R^3$, $R^4$, $R^5$, and $R^8$, each independently, are hydrogen, a linear alkyl radical having 1 to 50 carbon atoms, or a branched alkyl radical having 1 to 50 carbon atoms,
  $R^6$ is a chemical bond or $CH_2$, and
  $R^7$ is a linear alkylene radical having 1 to 50 carbon atoms or a branched alkylene radical having 1 to 50 carbon atoms.

8. The water-soluble or water-swellable polymer of claim 7, wherein the at least one structural unit of component d) is selected from at least one structural unit of the formula (5)

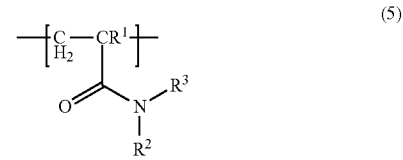

wherein
  $R^1$ is hydrogen, methyl or ethyl and
  $R^2$ and $R^3$, each independently, are hydrogen, methyl, ethyl, n-propyl or isopropyl, and at least one of the radicals $R^2$ and $R^3$ is not hydrogen, and at least one of the structural unit of the formula (6)

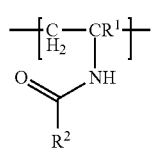 (6)

wherein

R¹ is hydrogen, methyl or ethyl and

R² is hydrogen, methyl, ethyl, n-propyl or isopropyl.

9. A process for preparing the water-soluble or water-swellable polymer of claim 1, wherein monomers from which the structural units of components a) to c) are derived are radically polymerized in a protic solvent, and optionally the monomers are neutralized before the polymerization or the polymer is neutralized after the polymerization, wherein the monomers and the polymer are neutralized with ammonia, organic amines, or a base, and wherein the base contains $Li^+$, $Na^+$, $K^+$, $Ca^{++}$, $Mg^{++}$, $Zn^{++}$ or $Al^{+++}$.

10. A cosmetic, dermatological or pharmaceutical composition comprising at least one water-soluble or water-swellable polymer of claim 1.

11. The composition of claim 10, wherein the composition is in the form of a fluid, gel, oil, foam, spray, lotion or cream.

12. The composition of claim 10 further comprising at least one surfactant.

13. The composition of claim 10, further comprising at least one substance selected from the group consisting of organic salts and inorganic salts.

14. The composition of claim 10, further comprising at least one substance selected from the group consisting of alpha-hydroxy acids and beta-hydroxy acids.

15. The composition of claim 10, further comprising at least one substance selected from the group consisting of vitamin C and vitamin C derivatives.

16. The composition of claim 10, further comprising at least one substance selected from the group consisting of benzoic acid, sorbic acid, salicylic acid, lactic acid, and para-methoxybenzoic acid.

17. The composition of claim 10, further comprising at least one substance selected from the group consisting of organic UV filters and inorganic UV filters.

18. The composition of claim 10, having a pH of 2 to 10.

19. The composition of claim 10, wherein the composition is in the form of a shower gel or shampoo.

20. A process for thickening, modifying the consistency, emulsifying, adding sensorial properties, solubilizing, dispersing, modifying lubricity, modifying adherency, stabilizing or modifying yield point formation of a cosmetic, dermatological or pharmaceutical composition comprising the step of adding at least one water-soluble or water-swellable polymer of claim 1, to the cosmetic, dermatological or pharmaceutical composition.

21. A process for thickening or forming a yield point in a cosmetic, dermatological or pharmaceutical composition comprising the step of adding at least one water-soluble or water-swellable polymer of claim 1, to the cosmetic, dermatological or pharmaceutical composition.

22. A process for thickening or forming a yield point in liquid compositions comprising one or more surfactants comprising the step of adding at least one water-soluble or water-swellable polymer of claim 1, to the liquid composition.

23. A process for stabilizing an emulsion, comprising the step of adding at least one water-soluble or water-swellable polymer of claim 1, to the emulsion.

\* \* \* \* \*